US011858127B2

(12) United States Patent
Sebring et al.

(10) Patent No.: US 11,858,127 B2
(45) Date of Patent: Jan. 2, 2024

(54) SYSTEM AND METHOD FOR MOUNTING A ROBOTIC ARM IN A SURGICAL ROBOTIC SYSTEM

(71) Applicant: Mobius Imaging, LLC, Shirley, MA (US)

(72) Inventors: Paul Sebring, Townsend, MA (US); Eugene Gregerson, Bolton, MA (US); Russell Stanton, Lunenberg, MA (US); Edward Daley, Maynard, MA (US); Gordon Row, Groton, MA (US)

(73) Assignee: Mobius Imaging, LLC, Shirley, MA (US)

(*) Notice: Subject to any disclaimer, the term of this patent is extended or adjusted under 35 U.S.C. 154(b) by 37 days.

(21) Appl. No.: 17/381,534

(22) Filed: Jul. 21, 2021

(65) Prior Publication Data

US 2021/0347036 A1   Nov. 11, 2021

Related U.S. Application Data

(63) Continuation of application No. 15/706,210, filed on Sep. 15, 2017, now Pat. No. 11,103,990.
(Continued)

(51) Int. Cl.
*B25J 5/04* (2006.01)
*A61B 34/30* (2016.01)
(Continued)

(52) U.S. Cl.
CPC ............... *B25J 5/04* (2013.01); *A61B 5/6835* (2013.01); *A61B 6/0407* (2013.01);
(Continued)

(58) Field of Classification Search
CPC ... B25J 5/04; B25J 5/007; B25J 9/0027; B25J 9/0096; B25B 11/00; B62B 3/002; B62B 3/104; B62B 2203/00–74
See application file for complete search history.

(56) References Cited

U.S. PATENT DOCUMENTS

| 5,799,055 A | 8/1998 | Peshkin et al. |
| 5,845,914 A | 12/1998 | Lenkman |

(Continued)

FOREIGN PATENT DOCUMENTS

| CN | 201422918 Y | 3/2010 |
| CN | 201542641 U | 8/2010 |

(Continued)

OTHER PUBLICATIONS

English language abstract and machine-assisted English translation for CN 101579269 extracted from espacenet.com database on Jan. 9, 2020, 8 pages.

(Continued)

*Primary Examiner* — Lee D Wilson
*Assistant Examiner* — Robert F Neibaur
(74) *Attorney, Agent, or Firm* — Howard & Howard Attorneys PLLC

(57) ABSTRACT

Systems and methods for mounting a robotic arm for use in robotic-assisted surgery, including a mobile shuttle that includes a support member for mounting the robotic arm that extends at least partially over a gantry of an imaging device.

(Continued)

Further embodiments include a mounting apparatus for mounting a robotic arm to a base or support column of an imaging device, to a patient table, to a floor or ceiling of a room, or to a cart that extends over the top surface of the patient table.

15 Claims, 22 Drawing Sheets

Related U.S. Application Data

(60) Provisional application No. 62/491,645, filed on Apr. 28, 2017, provisional application No. 62/426,491, filed on Nov. 26, 2016, provisional application No. 62/395,443, filed on Sep. 16, 2016.

(51) Int. Cl.
*A61B 34/20* (2016.01)
*A61B 34/00* (2016.01)
*A61B 90/00* (2016.01)
*A61B 90/50* (2016.01)
*A61B 6/04* (2006.01)
*A61B 5/00* (2006.01)
*A61B 6/00* (2006.01)
*B25J 5/00* (2006.01)
*B25J 9/00* (2006.01)
*B25J 9/16* (2006.01)
*A61B 90/57* (2016.01)

(52) U.S. Cl.
CPC .......... *A61B 6/4405* (2013.01); *A61B 6/4458* (2013.01); *A61B 34/00* (2016.02); *A61B 34/20* (2016.02); *A61B 34/30* (2016.02); *A61B 90/37* (2016.02); *A61B 90/50* (2016.02); *B25J 5/007* (2013.01); *B25J 9/0018* (2013.01); *B25J 9/0027* (2013.01); *B25J 9/0096* (2013.01); *B25J 9/1697* (2013.01); *A61B 2034/2055* (2016.02); *A61B 2090/3762* (2016.02); *A61B 2090/571* (2016.02); *Y10S 901/50* (2013.01)

(56) References Cited

U.S. PATENT DOCUMENTS

| | | | |
|---|---|---|---|
| 5,921,992 A | 7/1999 | Costales et al. | |
| 6,149,592 A | 11/2000 | Yanof et al. | |
| 6,236,875 B1 | 5/2001 | Bucholz et al. | |
| 6,275,725 B1 | 8/2001 | Cosman | |
| 6,533,455 B2 | 3/2003 | Graumann et al. | |
| 6,772,002 B2 | 8/2004 | Schmidt et al. | |
| 6,785,572 B2 | 8/2004 | Yanof et al. | |
| 6,933,695 B2 | 8/2005 | Blumenkranz | |
| 7,194,120 B2 | 3/2007 | Wicker et al. | |
| 7,251,522 B2 | 7/2007 | Bsenreiter et al. | |
| 7,587,235 B2 | 9/2009 | Wist et al. | |
| 7,699,877 B2 | 4/2010 | Davison | |
| 7,722,530 B2 | 5/2010 | Davison | |
| 7,799,036 B2 | 9/2010 | Davison et al. | |
| 8,016,835 B2 | 9/2011 | Birkmeyer et al. | |
| 8,046,054 B2 | 10/2011 | Kim et al. | |
| 8,118,488 B2 | 2/2012 | Gregerson | |
| 8,126,114 B2 | 2/2012 | Naylor et al. | |
| 8,394,144 B2 | 3/2013 | Zehavi et al. | |
| 8,454,583 B2 | 6/2013 | Perez-Cruet et al. | |
| 8,457,790 B2 | 6/2013 | Blondel et al. | |
| 8,509,503 B2 | 8/2013 | Nahum et al. | |
| 8,761,337 B2 | 6/2014 | Naylor et al. | |
| 8,795,188 B2 | 8/2014 | Maschke | |
| 8,974,460 B2 | 3/2015 | De la Fuente Klein et al. | |
| 9,125,680 B2 | 9/2015 | Kostrzewski et al. | |
| 9,237,861 B2 | 1/2016 | Nahum et al. | |
| 9,259,282 B2 | 2/2016 | Azizian et al. | |
| 9,283,048 B2 | 3/2016 | Kostrzewski et al. | |
| 9,308,050 B2 | 4/2016 | Kostrzewski et al. | |
| 9,545,233 B2 | 1/2017 | Sirpad et al. | |
| 9,550,299 B2 | 1/2017 | Wolf et al. | |
| 9,750,432 B2 | 9/2017 | Nahum et al. | |
| 9,833,292 B2 | 12/2017 | Kostrzewski et al. | |
| 10,004,562 B2 | 6/2018 | Kostrzewski et al. | |
| 10,039,476 B2 | 8/2018 | Nahum et al. | |
| 10,064,682 B2 | 9/2018 | Azizian et al. | |
| 10,076,385 B2 | 9/2018 | Shoham et al. | |
| 10,117,632 B2 | 11/2018 | Johnson et al. | |
| 10,118,005 B2 * | 11/2018 | Yoo | C12N 5/0656 |
| 10,136,952 B2 | 11/2018 | Couture et al. | |
| 10,137,566 B2 * | 11/2018 | Bastian, II | B25J 5/007 |
| 10,159,534 B2 | 12/2018 | Maillet et al. | |
| 10,500,015 B2 | 12/2019 | Taylor et al. | |
| 10,596,705 B2 | 3/2020 | Gombert et al. | |
| 10,932,867 B2 | 3/2021 | Park | |
| 2007/0156157 A1 | 7/2007 | Nahum et al. | |
| 2012/0241576 A1 | 9/2012 | Yu | |
| 2013/0345718 A1 | 12/2013 | Crawford et al. | |
| 2014/0003572 A1 | 1/2014 | Gregerson et al. | |
| 2014/0005678 A1 | 1/2014 | Shelton, IV et al. | |
| 2014/0139215 A1 | 5/2014 | Gregerson et al. | |
| 2014/0188132 A1 | 7/2014 | Kang | |
| 2014/0249546 A1 * | 9/2014 | Shvartsberg | A61B 90/50 |
| | | | 606/130 |
| 2014/0265182 A1 | 9/2014 | Stanton et al. | |
| 2014/0265253 A1 | 9/2014 | Ingrasci | |
| 2014/0275953 A1 | 9/2014 | Gregerson et al. | |
| 2015/0202009 A1 | 7/2015 | Nussbaumer et al. | |
| 2015/0366624 A1 | 12/2015 | Kostrzewski et al. | |
| 2016/0030117 A1 | 2/2016 | Mewes | |
| 2016/0081754 A1 | 3/2016 | Kostrzewski et al. | |
| 2016/0174914 A1 | 6/2016 | Lerch et al. | |
| 2016/0220320 A1 | 8/2016 | Crawford et al. | |
| 2016/0235492 A1 | 8/2016 | Morard et al. | |
| 2016/0278875 A1 | 9/2016 | Crawford et al. | |
| 2017/0071691 A1 | 3/2017 | Crawford et al. | |
| 2017/0079727 A1 | 3/2017 | Crawford et al. | |
| 2017/0172669 A1 | 6/2017 | Berkowitz et al. | |
| 2017/0231702 A1 | 8/2017 | Crawford et al. | |
| 2017/0239002 A1 | 8/2017 | Crawford et al. | |
| 2017/0239003 A1 | 8/2017 | Crawford et al. | |
| 2017/0239006 A1 | 8/2017 | Crawford et al. | |
| 2017/0245951 A1 | 8/2017 | Crawford et al. | |
| 2017/0252112 A1 | 9/2017 | Crawford et al. | |
| 2017/0258533 A1 | 9/2017 | Crawford et al. | |
| 2017/0258535 A1 | 9/2017 | Crawford et al. | |
| 2017/0312039 A1 | 11/2017 | Crawford et al. | |
| 2017/0348061 A1 | 12/2017 | Joshi et al. | |
| 2017/0360513 A1 | 12/2017 | Amiot et al. | |
| 2017/0360517 A1 | 12/2017 | Crawford et al. | |
| 2018/0000546 A1 | 1/2018 | Crawford et al. | |
| 2018/0078439 A1 | 3/2018 | Cagle et al. | |
| 2018/0110573 A1 | 4/2018 | Kostrzewski | |
| 2018/0116739 A1 | 5/2018 | Gogarty et al. | |
| 2018/0116740 A1 | 5/2018 | Gogarty et al. | |
| 2018/0125597 A1 | 5/2018 | Gogarty et al. | |
| 2018/0157238 A1 | 6/2018 | Gogarty et al. | |
| 2018/0207794 A1 | 7/2018 | Sebring et al. | |
| 2018/0221098 A1 | 8/2018 | Forsyth et al. | |
| 2018/0235715 A1 | 8/2018 | Amiot et al. | |
| 2018/0250077 A1 | 9/2018 | Xu et al. | |
| 2018/0256259 A1 | 9/2018 | Crawford | |
| 2018/0271605 A1 | 9/2018 | Kostrzewski et al. | |
| 2018/0346008 A1 | 12/2018 | Nahum et al. | |
| 2019/0000561 A1 | 1/2019 | Decker et al. | |
| 2019/0000569 A1 | 1/2019 | Crawford et al. | |
| 2019/0021795 A1 | 1/2019 | Crawford et al. | |
| 2019/0021799 A1 | 1/2019 | Crawford et al. | |
| 2019/0021800 A1 | 1/2019 | Crawford et al. | |
| 2019/0029759 A1 | 1/2019 | Mcdonell | |
| 2019/0029765 A1 | 1/2019 | Crawford et al. | |
| 2019/0038362 A1 | 2/2019 | Nash et al. | |
| 2019/0053859 A1 | 2/2019 | Couture et al. | |
| 2019/0069961 A1 | 3/2019 | Smith et al. | |
| 2019/0099222 A1 | 4/2019 | Nahum et al. | |

(56) References Cited

U.S. PATENT DOCUMENTS

| | | |
|---|---|---|
| 2019/0117313 A1 | 4/2019 | Crawford |
| 2019/0142533 A1 | 5/2019 | Itkowitz et al. |
| 2019/0239964 A1 | 8/2019 | Leboeuf, II et al. |
| 2019/0269467 A1 | 9/2019 | Forsyth et al. |
| 2019/0274765 A1 | 9/2019 | Crawford et al. |
| 2020/0170539 A1 | 6/2020 | Sayler et al. |
| 2020/0170720 A1 | 6/2020 | Ummalaneni |
| 2020/0179067 A1 | 6/2020 | Ross et al. |

FOREIGN PATENT DOCUMENTS

| | | |
|---|---|---|
| CN | 101700184 B | 1/2011 |
| CN | 101579269 B | 4/2011 |
| CN | 101853333 B | 11/2012 |
| EP | 1103223 A2 | 5/2001 |
| WO | 2015115809 A1 | 8/2015 |
| WO | 2015142907 A1 | 9/2015 |
| WO | 2015142943 A1 | 9/2015 |
| WO | 2016168671 A1 | 10/2016 |
| WO | 2017036340 A1 | 3/2017 |
| WO | 2017122202 A1 | 7/2017 |
| WO | 2018185729 A1 | 10/2018 |

OTHER PUBLICATIONS

English language abstract and machine-assisted English translation for CN 101700184 extracted from espacenet.com database on Jan. 9, 2020, 10 pages.

English language abstract and machine-assisted English translation for CN 101853333 extracted from espacenet.com database on Jan. 9, 2020, 9 pages.

English language abstract and machine-assisted English translation for CN 201422918 extracted from espacenet.com database on Jan. 9, 2020, 7 pages.

English language abstract and machine-assisted English translation for CN 201542641 extracted from espacenet.com database on Jan. 9, 2020, 10 pages.

English language abstract and machine-assisted English translation for WO 2015/115809 extracted from espacenet.com database on Jan. 9, 2020, 8 pages.

English language abstract for WO 2017/036340 extracted from espacenet.com database on Jan. 9, 2020, 2 pages.

International Search Report for Application No. PCT/US2017/051806 dated Feb. 13, 2018, 5 pages.

Pal jug, Eric et al. "The JPL Serpentine Robot: a 12 DOF System for Inspection", NASA JPL Technical Reports Server, https://trs.jpl.nasa.gov/handle/2014/29159, Jan. 1, 1995, 5 pages.

\* cited by examiner

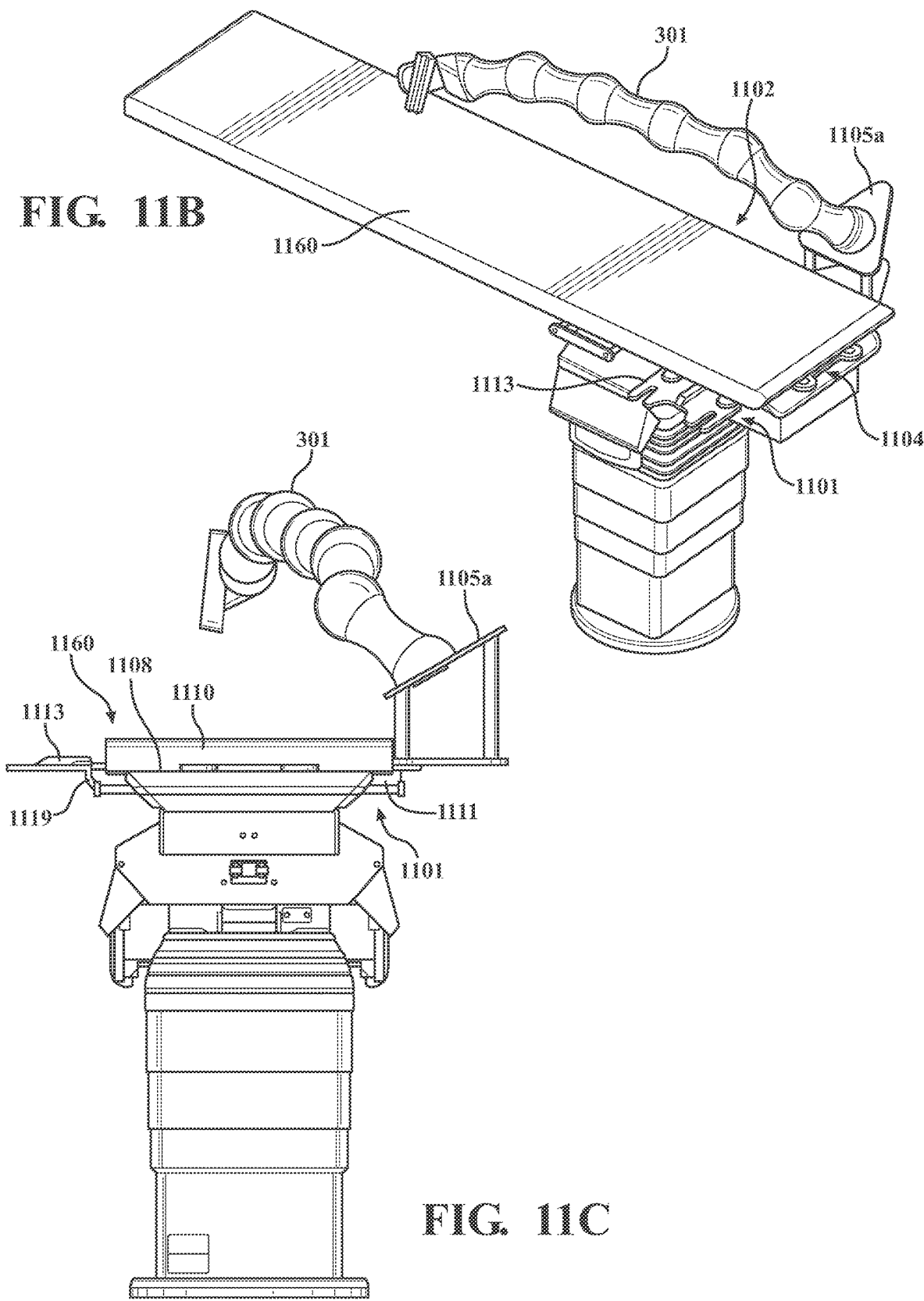

SYSTEM AND METHOD FOR MOUNTING A ROBOTIC ARM IN A SURGICAL ROBOTIC SYSTEM

CROSS-REFERENCE TO RELATED APPLICATIONS

This application is a Continuation of U.S. patent application Ser. No. 16/706,210, filed on Sep. 15, 2017, which claims the benefit of priority to U.S. Provisional Application No. 62/395,443, filed on Sep. 16, 2016, U.S. Provisional Application No. 62/426,491, filed on Nov. 26, 2016, and U.S. Provisional Application No. 62/491,645, filed Apr. 28, 2017, the entire contents of all of which are incorporated by reference herein.

BACKGROUND

Robotically-assisted surgical procedures have attracted increased interest in recent years. Robot assisted surgery, including robotically-assisted minimally-invasive surgical procedures, can be faster, safer and require less recovery time than conventional open surgeries. Surgical robotic systems are typically large devices that approach the patient from the side and may take up a relatively large amount of space in the surgical area. There is a continuing need for improvement to the usability and effectiveness of surgical robotic systems.

SUMMARY

Various embodiments include systems and methods for mounting a robotic arm for use in robotic-assisted surgery.

Embodiments include a mobile shuttle for mounting at least one robotic arm proximate to an imaging device that includes a mobile base configured to move the shuttle to a position adjacent to the imaging device, and a support member for mounting at least one robotic arm, the support member supported by the mobile base and extending at least partially over a gantry of the imaging device when the shuttle is moved to the position adjacent to the imaging device.

Further embodiments include a mounting apparatus for a robotic arm that includes a base portion that is supported on a base of an imaging system, and a support member that extends from the base portion over a top surface of a patient table, the support member including a mounting surface for a robotic arm.

Further embodiments include a mobile mounting apparatus for a robotic arm that includes a base portion, a pair of support arms extending upwards from the base, and a support member for mounting at least one robotic arm, the support member extending between the support arms, where an open region is defined between the base portion, the pair of support arms and the support member and the open region is sized and shaped to accommodate a surgical table within the open region.

Further embodiments include a mounting apparatus for a robotic arm that includes a base portion, a support member that is supported by the base portion and includes a mounting surface for a robotic arm, and an anchoring apparatus that is selectively deployable from the base portion, the anchoring apparatus including at least one plate-shaped element coupled to the base portion and lying flat against the floor when deployed such that a weight may be provided on the top surface of the at least one plate-shaped element to improve the stability of the mounting apparatus.

Further embodiments include a mounting apparatus for a robotic arm that includes a mobile base, a support member that is supported by the base and includes a mounting surface for a robotic arm, and a docking system having a first docking element on the base that selectively engages with a second docking element that is pre-installed on a floor to maintain the mobile base and support member at a fixed location on the floor.

Further embodiments include a mounting apparatus for mounting a robotic arm to a surgical table that includes a plate member that extends across the width of a tabletop of the surgical table, a clamping mechanism that clamps the plate member to the surgical table, and a mounting surface coupled to and raised from the plate member that is configured to support a base end of a surgical robotic arm.

Further embodiments include a mounting apparatus for mounting a robotic arm to a surgical table that is supported above a floor by a column, the mounting apparatus including a support element that is fixed to the column beneath the surgical table, and a support arm that extends up from the support element above the surface of the surgical table, the support arm including a mounting surface for a surgical robotic arm.

Further embodiments include a ceiling mount for a surgical robotic arm that includes a support member that extends vertically downward from the ceiling, the support member having a mounting surface for a surgical robotic arm.

BRIEF DESCRIPTION OF THE DRAWINGS

Other features and advantages of the present invention will be apparent from the following detailed description of the invention, taken in conjunction with the accompanying drawings of which:

FIGS. 11A-11E illustrate a first embodiment table mount for a robotic arm used for robotically assisted surgery.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1A:
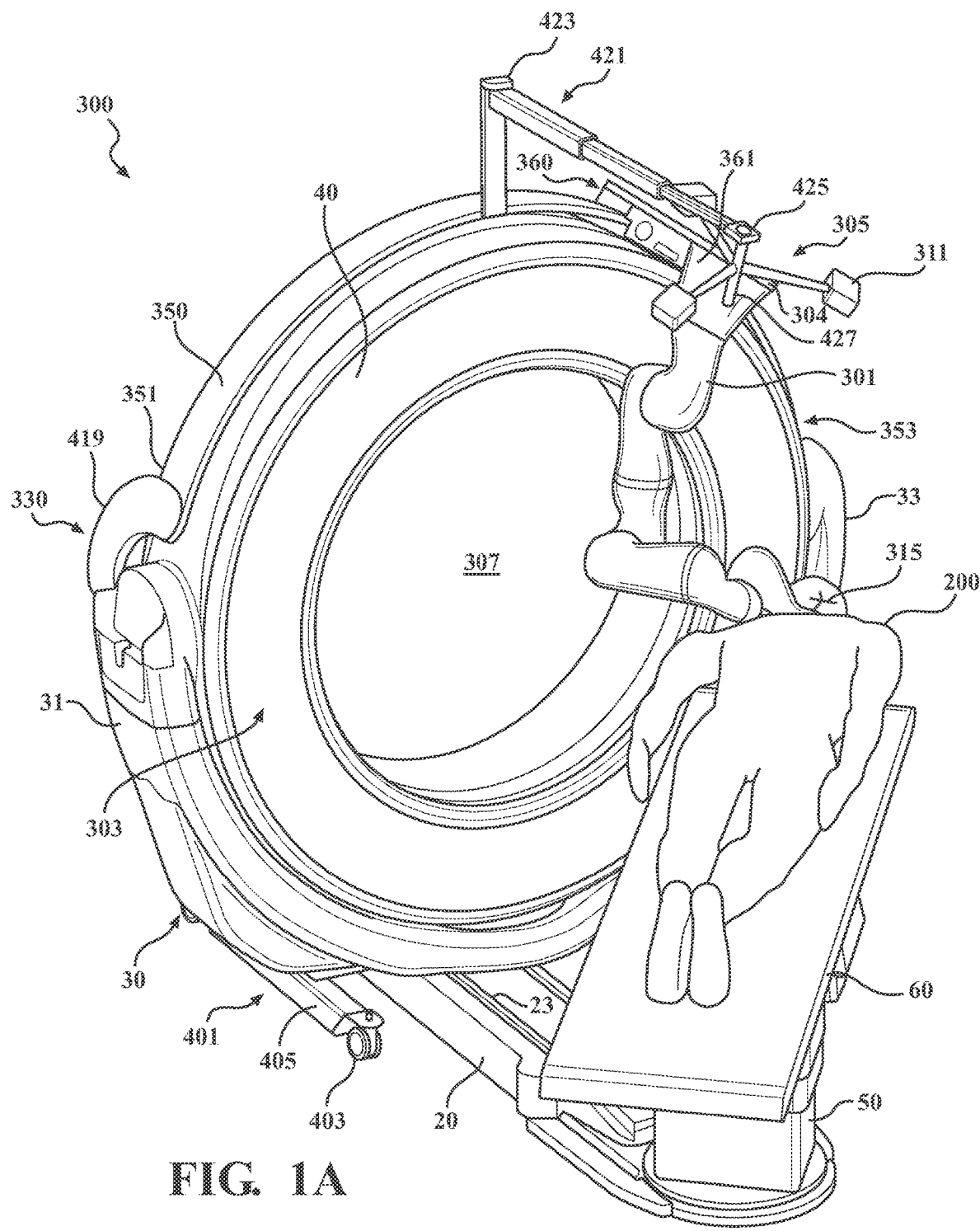
FIGS. 1A-1D illustrate a robotically-assisted surgical system including a mobile shuttle according to an embodiment.
Figure 1B:
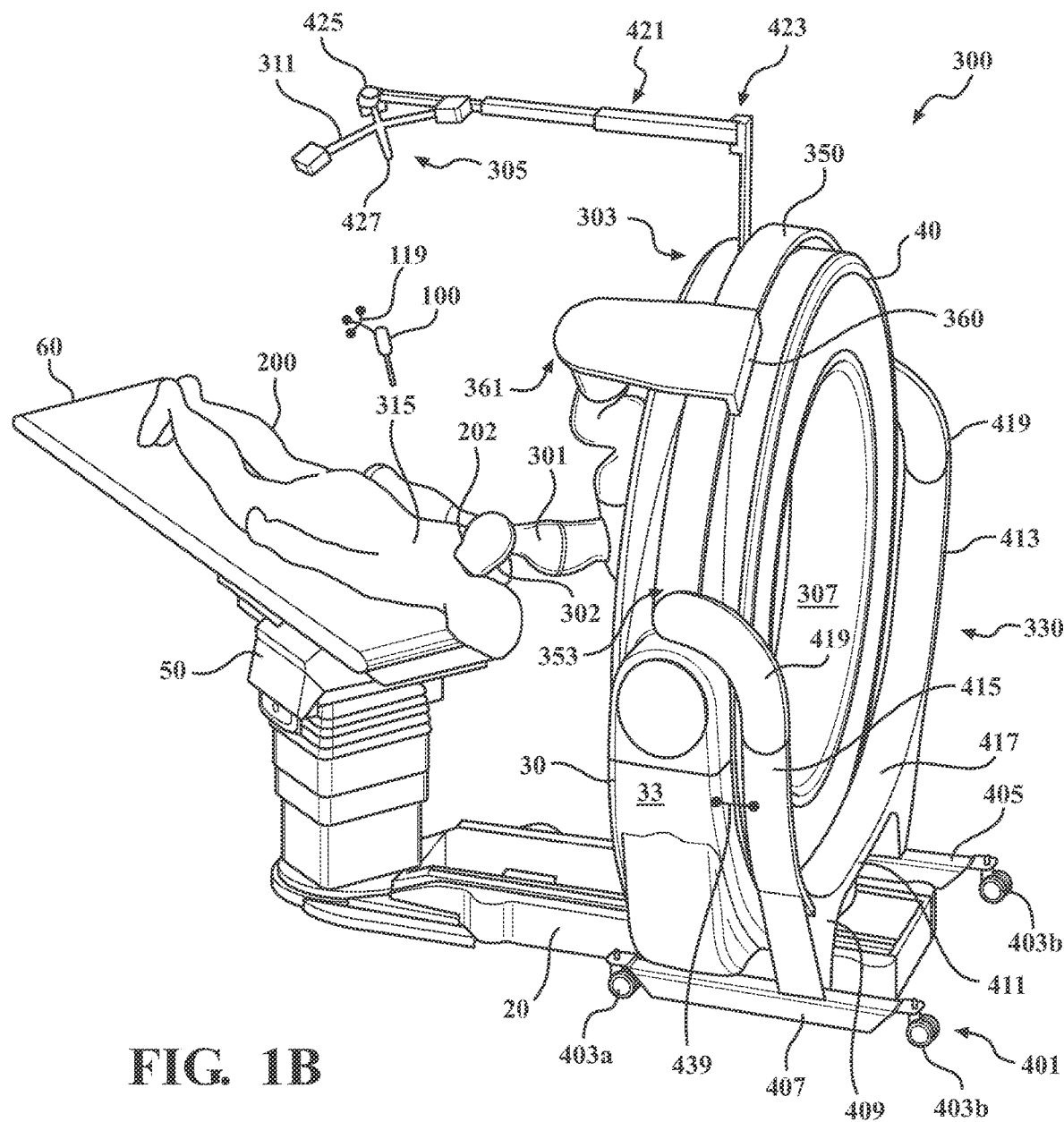
Figure 1C:
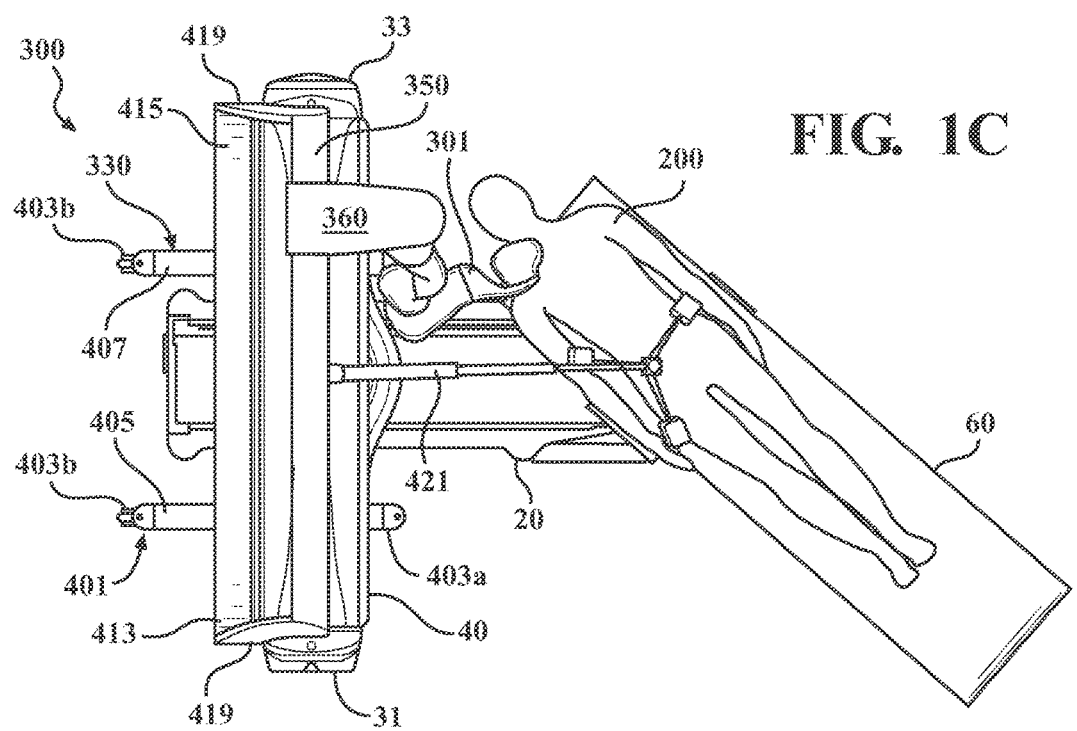
Figure 1D:
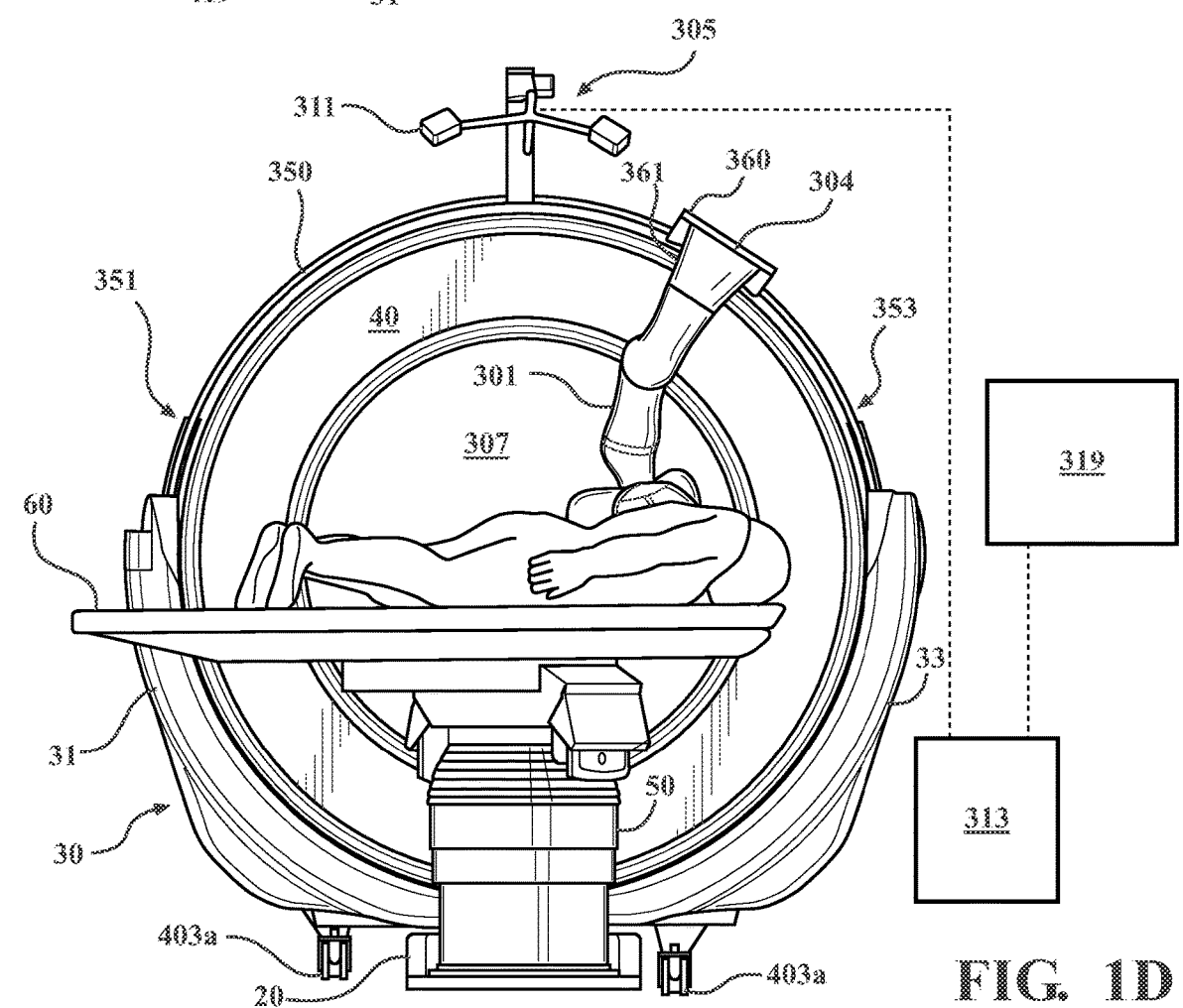

FIGS. 1A-1D illustrate a system 300 for performing robotically-assisted image-guided surgery according to various embodiments. FIG. 1A is a front perspective view of the system 300 and FIG. 1B is a rear perspective view of the system 300. FIG. 1C is a top view of the system 300 and FIG. 1D is a front elevation view of the system 300. The system 300 in this embodiment includes a robotic arm 301, an imaging device 303 and a motion tracking system 305. The robotic arm 301 may comprise a multi-joint arm that includes a plurality of linkages connected by joints having actuator(s) and optional encoder(s) to enable the linkages to bend, rotate and/or translate relative to one another in response to control signals from a robot control system. The robotic arm 301 may be fixed to a support member 350 at one end and may have an end effector 302 at the other end of the robotic arm 301. The end effector 302 may be most clearly seen in FIGS. 1B and 3. Although a single robotic arm 301 is shown in FIGS. 1A-1D, it will be understood that the system 300 may include multiple robotic arms attached to suitable support structure(s).

The robotic arm 301 may aid in the performance of a surgical procedure, such as a minimally-invasive spinal surgical procedure or various other types of orthopedic, neurological, cardiothoracic and general surgical procedures. In the embodiment of FIGS. 1A-1B, the robotic arm 301 may be used to assist a surgeon performing a surgical procedure in a cervical spinal region of a patient. The robotic arm 301 may also be used for thoracic and/or lumbar spinal procedures. The procedures may be performed posteriorly, anteriorly or laterally.

In embodiments, the robotic arm 301 may be controlled to move the end effector 302 to one or more pre-determined positions and/or orientations with respect to a patient 200. In some embodiments, the end effector 302 may be or may have attached to it an invasive surgical tool, such as a needle, a cannula, a dilator, a cutting or gripping instrument, a drill, a screw, an electrode, an endoscope, an implant, a radiation source, a drug, etc., that may be inserted into the body of the patient. In other embodiments, the end effector 302 may be a hollow tube or cannula that may receive an invasive surgical tool 100 (see FIG. 1B), including without limitation a needle, a cannula, a tool for gripping or cutting, an electrode, an implant, a radiation source, a drug and an endoscope. The invasive surgical tool 100 may be inserted into the patient's body through the hollow tube or cannula by a surgeon. The robotic arm 301 may be controlled to maintain the position and orientation of the end effector 302 with respect to the patient 200 to ensure that the surgical tool(s) 100 follow a desired trajectory through the patient's body to reach a target area. The target area may be previously-determined during a surgical planning process based on patient images, which may be obtained using the imaging device 303.

The imaging device 303 may be used to obtain diagnostic images of a patient 200, which may be a human or animal patient. In embodiments, the imaging device 303 may be an x-ray computed tomography (CT) imaging device. The patient 200 may be positioned within a central bore 307 of the imaging device 303 and an x-ray source and detector may be rotated around the bore 307 to obtain x-ray image data (e.g., raw x-ray projection data) of the patient 200. The collected image data may be processed using a suitable processor (e.g., computer) to perform a three-dimensional reconstruction of the object. In other embodiments, the imaging device 303 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure) or intra-operatively (i.e., during a surgical procedure) by positioning the patient 200 within the bore 307 of the imaging device 303. In the system 300 of FIGS. 1A-1D, this may be accomplished by moving the imaging device 303 over the patient 200 to perform a scan while the patient 200 may remain stationary. The imaging device 303 may also be used to validate a surgical intervention, such as by determining that an invasive tool, instrument and/or implant has been placed in the proper location in the patient's body.

Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182 and U.S. Patent Application Publication No. 2014/0275953, the entire contents of all of which are incorporated herein by reference. In the embodiment shown in FIGS. 1A-1D, the patient support 60 (e.g., surgical table) upon which the patient 200 may be located is secured to the imaging device 303, such as via a column 50 which is mounted to a base 20 of the imaging device 303. In the embodiment of FIGS. 1A-1D, the patient 200 is supported on a patient table 60 that is rotated away from the bore 307 of the imaging device 303. During an imaging scan, the patient support 60 may be rotated in-line with the bore 307 such that the patient axis is aligned with the imaging axis of the imaging device 303. A portion of the imaging device 303 (e.g., an O-shaped imaging gantry 40) which includes at least one imaging component may translate along the length of the base 20 on rails 23 to perform an imaging scan of the patient 200, and may translate away from the patient 200 to an out-of-the-way positon for performing a surgical procedure on the patient 200.

An example imaging device 303 that may be used in various embodiments is the AIRO® intra-operative CT system manufactured by Mobius Imaging, LLC and distributed by Brainlab, AG. Other imaging devices may also be utilized. For example, the imaging device 303 may be a mobile CT device that is not attached to the patient support 60 and may be wheeled or otherwise moved over the patient 200 and the support 60 to perform a scan. Examples of mobile CT devices include the BodyTom® CT scanner from Samsung Electronics Co., Ltd. and the O-arm® surgical imaging system form Medtronic, plc. The imaging device 303 may also be a C-arm x-ray fluoroscopy device. In other embodiments, the imaging device 303 may be a fixed-bore imaging device, and the patient 200 may be moved into the bore of the device, either on a surgical support 60 as shown in FIGS. 1A-1D, or on a separate patient table that is configured to slide in and out of the bore.

The motion tracking system 305 in this embodiment includes a plurality of marker devices 119, 202 and 315 and a stereoscopic optical sensor device 311 that includes two or more cameras (e.g., IR cameras). The optical sensor device 311 may include one or more radiation sources (e.g., diode ring(s)) that direct radiation (e.g., IR radiation) into the surgical field, where the radiation may be reflected by the marker devices 119, 202 and 315 and received by the cameras. A computer 313 may be coupled to the sensor device 311 as schematically illustrated in FIG. 1D and may determine the positions and orientations of the marker devices 119, 202, 315 detected by the cameras using, for example, triangulation techniques. A 3D model of the surgical space may be generated and continually updated using motion tracking software implemented by the computer 313. In embodiments, the computer 313 may also receive image data from the imaging device 303 and may register the image data to a common coordinate system with the motion tracking system 305 using image registration techniques as are known in the art. In embodiments, a reference marker device 315 (e.g., reference arc) may be rigidly attached to a landmark in the anatomical region of interest (e.g., clamped or otherwise attached to the spinous process of a patient's vertebrae) to enable the anatomical region of interest to be continually tracked by the motion tracking system 305. Another marker device 202 may be rigidly attached to the robotic arm 301, such as on the end effector 302 of the robotic arm 301, to enable the position of robotic arm 301 and end effector 302 to be tracked using the motion tracking system 305. The computer 313 may include software configured to perform a transform between the joint coordinates of the robotic arm 301 and the common coordinate system of the motion tracking system 305, which may enable the position and orientation of the end effector 302 of the robotic arm 301 to be controlled with respect to the patient 200.

In addition to passive marker devices described above, the motion tracking system 305 may alternately utilize active marker devices that may include radiation emitters (e.g., LEDs) that may emit radiation that is detected by an optical sensor device 311. Each active marker device or sets of active marker devices attached to a particular object may emit radiation in a pre-determined strobe pattern (e.g., with modulated pulse width, pulse rate, time slot and/or amplitude) and/or wavelength which may enable different objects to be uniquely identified and tracked by the motion tracking system 305. One or more active marker devices may be fixed relative to the patient, such as on a reference marker device as described above or secured to the patient's skin via an adhesive membrane or mask. Additional active marker devices may be fixed to surgical tools 100 and/or to the end effector 302 of the robotic arm 301 to allow these objects to be tracked relative to the patient.

In further embodiments, the marker devices may be passive maker devices that include moiré patterns that may enable their position and orientation to be tracked in three-dimensional space using a single camera using Moiré Phase Tracking (MPT) technology. Other tracking technologies, such as computer vision systems and/or magnetic-based tracking systems, may also be utilized.

The system 300 may also include a display device 319 as schematically illustrated in FIG. 1D. The display device 319 may display image data of the patient's anatomy obtained by the imaging device 303. The display device 319 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 305 may be shown on the display 319, and may be shown superimposed with the image data. For example, the position and/or orientation of an implantable surgical tool 100 with respect to the patient's anatomy may be graphically depicted on the display 319 based on the tracked position/orientation of the marker device 119 fixed to the tool 100 and the known geometry of the tool 100, which may be pre-registered with the motion tracking system 305. The display 319 may also include graphical depictions of other objects, such as implants (e.g., pedicle screws).

In various embodiments, the imaging device 303 may be located close to the surgical area of the patient 200 which may enable pre-operative, intra-operative and post-operative imaging of the patient 200, preferably without needing to remove the patient from the operating theater or transitioning the patient from the surgical table 60. In embodiments, the imaging device 303 may be located less than about 5 meters, such as less than about 2 meters (e.g., less than about 1 meter) from the surgical area of the patient 200 during a surgical procedure. As shown, for example, in FIGS. 1A-1D, the imaging device 303 (e.g., X-ray CT scanner) may include an imaging gantry 40 that may be moved (i.e., translated) over the surgical area of patient 200 to perform an imaging scan and may be moved (i.e., translated) away from the surgical area of the patient 200 so as not to interfere with a surgeon performing a surgical procedure. In the embodiment shown in FIG. 1, the imaging gantry 40 may be supported by a gimbal support 30, which may include a pair of arms 31, 33 extending upwards from the base 20 which may each attach to opposite sides of the gantry 40. The gimbal 30 and the gantry 40 may translate together along the length of the base 20 to perform an imaging scan. In some embodiments, the gantry 40 may be attached to the arms 31, 33 of the gimbal 30 by rotary bearings which may enable the gantry 40 to tilt with respect to the gimbal 30 and the base 20 to obtain patient images at an oblique angle.

In various embodiments, the robotic arm 301 may be attached to a support structure that is also located close to the surgical area of the patient 200. For example, the base end 304 of the robotic arm 301 (i.e., the end of the arm 301 opposite the end effector 302) may be fixed to a support structure at a position that is less than about 2 meters, such as less than about 1 meter (e.g., between 0.5 and 1 meter) from the surgical area of the patient 200 during a surgical procedure.

In a conventional robotically-assisted surgical system, a robotic arm may be mounted to a mobile cart that may be moved proximate to the surgical area of the patient 200, typically approaching the surgical table 60 from a side of the table 60. The cart may remain fixed in place adjacent to the surgical table 60 while a robotic arm may extend from the cart into the surgical area during a surgical procedure. Alternately, the mobile cart may be used primarily for transport of the robotic arm to and from a position proximate to the surgical area. During surgery, the robotic arm may be attached to another support structure, such as a surgical side rail of the patient table 60, and the cart may be moved out of the way. In either case, the robotic arm and/or cart may occupy a relatively large amount of space in the surgical area. For example, the robotic arm may take up space that would otherwise by occupied by a surgeon or other clinician during the surgical procedure, which may impede workflow.

In addition, the robotic arm and/or cart will often be positioned so as to impede imaging of the patient by an imaging device 303. For example, a robotic arm and/or cart positioned along a side of the patient table 60 may not fit within the bore 307 of the gantry 40 of the imaging device 303, and may need to be removed prior to imaging of the patient 200.

In the embodiment of FIGS. 1A-1D, the robotic arm 303 may be mounted to a mobile shuttle 330 having a support member 350 for a robotic arm 301 that may extend at least partially over an outer surface (e.g., circumference) of the gantry 40 of the imaging system 303 when the shuttle 330 is moved adjacent to the imaging system 303. In the embodiment of FIG. 1, the support member 350 comprises a curved rail that extends around the outer circumference of the gantry 40. The support member 350 may extend around at least about 25%, such as between about 30-50% of the outer circumference of the gantry 40. The support member 350 may extend around at least a portion of the outer circumference of the gantry 40 that is located above the surgical area of the patient 200. In the embodiment of FIG. 1, the support member 350 forms a semicircular arc that extends between a first end 351, which is located proximate to the end of a first arm 31 of the gimbal 30, and a second end 353, which is located proximate to the end of a second arm 33 of the gimbal 30 when the shuttle 330 is positioned adjacent to the imaging system 303. The semicircular arc support member 350 may be concentric with the outer circumference of the gantry 40. In embodiments, the support member 350 may extend along a semicircular arc having a radius that is greater than about 33 inches, such as greater than about 35 inches (e.g., between 33 and 50 inches). The support member 350 may be spaced from the outer surface of the gantry 40 by a pre-determined distance, which may be from less than an inch (e.g., 0.5 inches) to 6 or 10 inches or more. In some embodiments, the support member 350 may be spaced from the gantry 40 by an amount sufficient to enable the tilt motion of the gantry 40 with respect to the gimbal 30 over at least a limited range of motion.

In addition to a curved support member 350, in some embodiments the support member 350 may comprise one or more straight segments (e.g., rail segments), where at least a portion of the support member 350 may extend over the top surface of the gantry 40.

A carriage 360 may be located on the support member 350 and may include a mounting surface 361 for mounting the base end 304 of the robotic arm 301 to the carriage 360. As shown in FIG. 1A-1D, the carriage 360 may extend from the support member 350 towards a first (e.g., front) face of the gantry 40. The mounting surface 361 for the robotic arm 301 may extend beyond the first (e.g., front) face of the gantry 40 and the robotic arm 301 may extend over the first (e.g., front) face of the gantry 40. In some embodiments, the configuration of the carriage 360 and mounting surface 361 may be reversed such that the mounting surface 361 extends beyond the second (e.g., rear) face of the gantry 40, and the robotic arm 301 may extend over the second (e.g., rear) face of the gantry 40. In this configuration, the patient support 60 may be configured such that the patient support 60 and patient 200 extend into or through the bore 307 of the gantry 40, and a portion of the patient 200 requiring surgical intervention (e.g., the cranium) may be accessed from the second (e.g., rear) side of the gantry 40.

In some embodiments, the carriage 360 and the robotic arm 301 attached thereto may be moved to different positions along the length of support member 350 (e.g., any arbitrary position between the first end 351 and the second end 353 of the support member 360). The carriage 360 and the robotic arm 301 may be fixed in place at a particular desired position along the length of the support member 350. In some embodiments, the carriage 360 may be moved manually (e.g., positioned by an operator at a particular location along the length of the support member 350 and then clamped or otherwise fastened in place). Alternately, the carriage 360 may be driven to different positions using a suitable drive mechanism (e.g., a motorized belt drive, friction wheel, gear tooth assembly, cable-pulley system, etc., not shown in FIGS. 1A-1D). The drive mechanism may be located on the carriage 360 and/or the support member 350, for example. An encoder mechanism may be utilized to indicate the position of the carriage 360 and the base end 304 of the robotic arm 301 on the support member 350. Although the embodiment of FIGS. 1A-1D illustrate one robotic arm 301 mounted to the support member 350, it will be understood that more than one robotic arm may be mounted to the support member 350 via respective carriages 360.

Further, in some embodiments, the robotic arm 301 may be mounted directly to the support member 350, such as on a mounting surface 361 that is integrally formed on the support member 350. In such an embodiment, the position of robotic arm 301 may not be movable along the length of the support member 350.

In some embodiments, there may be sufficient clearance between the support member 350 and/or carriage 360 and the outer circumference of the gantry 40 to enable the shuttle 330 with the robotic arm 301 attached to approach the imaging system 303 from the second (e.g., rear) side of the imaging system 303 such that the robotic arm 101 may pass over the outer circumference of the gantry 40 and then extend over the front side of the gantry 40 in a configuration such as shown in FIGS. 1A-1D. In embodiments, the robotic arm 301 may be in a first pose in order to reduce its profile in the radial direction as it passes over the gantry 40 and may then be extended in a direction towards the patient 200 as shown in FIGS. 1A-1D. Alternately or in addition, the carriage 360 may be hinged to enable the mounting surface 361 to be pivoted upwards to provide additional clearance for the robotic arm 301 to pass over the gantry 40 when the mobile shuttle 330 is positioned adjacent to the imaging system 303 and may then be pivoted downward to the configuration shown in FIGS. 1A-1D. In some embodiments, the height of the support member 350 may be temporarily raised, such as via a jack mechanism on the mobile shuttle 330, to allow the robotic arm 301 to pass over the gantry 40, and may then be lowered to the configuration shown in FIGS. 1A-1D. In further embodiments, the support member 350 may be moved over the gantry 40 without the robotic arm 301 or the carriage 360 mounted to the support member 350, and the robotic arm 301 or the carriage 360 may be mounted to the support member 350 after the mobile shuttle 330 is moved into position adjacent to the imaging system 303. In some embodiments, the robotic arm 303 may be mounted to the carriage 360 via an adaptor, which may be a quick-connect/disconnect adaptor.

In some embodiments, the robotic arm 301 may be mounted to a mounting surface 361 that is located on a top surface of the carriage 360 to enable the robotic arm 301 to pass over the gantry 40, such as shown in the embodiment of FIGS. 4A-4D, described below.

The mobile shuttle 330 further includes a base 401 having a plurality of wheels 403 attached to the base 401 that enable the mobile shuttle 330 to be moved over a surface (e.g., a floor). In the embodiment of FIGS. 1A-1D, the base 401 includes two sets of wheels 403, including a first set of wheels 403a located proximate to a first end 402 the mobile shuttle 330 and a second set of wheels 403b located proximate to a second end 404 of the mobile shuttle 330. The wheels 403 may be positioned and distributed to provide balance and stability to the mobile shuttle 330 and may enable the shuttle to be moved, with or without one or more robotic arms 301 attached, without tipping over. In the embodiment of FIGS. 1A-1D, each of the wheels 403 of the mobile shuttle are located in a caster assembly, which may be a swivel-type caster assembly to provide increased maneuverability of the shuttle 330. However, it will be understood that other configurations for the wheels 403 may be utilized. In some embodiments, at least a portion of the wheels 403 may be geared into a drive mechanism for propelling the mobile shuttle 330 over a surface.

The base 401 of the mobile shuttle 330 may include two parallel rails 405, 407, where each of the wheels 403 may be mounted to a rail 405, 407. The rails 405, 407 may be separated from each other by a distance that is greater than a width of the base 20 of the imaging system 303. In one embodiment, the rails 405, 407 are separated by at least about 22 inches. When the mobile shuttle 330 is moved adjacent to the imaging system 303 as shown in FIGS. 1A-1D, the rails 405, 407 may extend at least partially along opposing sides of the base 20 of the imaging system 303. The rails 405, 407 may have a top surface that is less than a foot from the floor, and preferably less than about 8 inches from the floor. As shown in FIGS. 1A-1D, the height of the rails 405, 407 may enable the rails 405, 407 to move under and fit beneath a portion of the imaging system 303, such as the arms 31, 33 of the gimbal 30 of the imaging system 303.

A connecting member 409 which may extend generally transverse to the rails 405, 407 may connect the rails 405, 407 to each other. The connecting member 409 may be located closer to the second end 404 of the shuttle 330 than to the first end 402, as shown in FIG. 1B. In embodiments, the connecting member 409 may extend upwards from each of the rails 405, 407 to form a bridge portion 411, as shown in FIG. 1B. The bridge portion 411 may have sufficient clearance to extend over the base 20 of the imaging system 303, as shown in FIG. 1B. In embodiments, the bridge portion 411 may have a clearance height of at least about 7 inches (e.g., 8-12 inches). The height of the bridge portion 411 may be such that it does not interfere with the tilt motion of the gantry 40.

At least one arm 413, 415 may extend upwards from the base 401 of the mobile shuttle 330. As shown in FIG. 1B, a pair of arms 413, 415 may extend from respective rails 405, 407 of the base 401. In other embodiments, at least one arm 413, 415 may extend from the connecting member 409. Each of the arms 413, 415 may have a shape that substantially corresponds to the shape of the respective arms 31, 33 of the gimbal 30 which supports the gantry 40 of the imaging system 303. When the mobile shuttle 330 is moved adjacent to the imaging system 303 as shown in FIGS. 1A-1D, the arms 413, 415 may extend adjacent to the arms 31, 33 of the gimbal 30. The arms 413, 415 may have a curved profile over at least a portion of their length, where the shape of the curve may substantially correspond to the shape of the outer circumference of the O-shaped gantry 40. The arms 413, 415 may be located radially-outwards from the outer circumference of the gantry 40, which may enable the gantry 40 to tilt on the gimbal 30. In some embodiments, a width of the mobile shuttle 330 defined between the outer surfaces of the arms 413, 415 may be less than a width of the imaging system 303, which may be defined by external surfaces of the arms 31, 33 of the gimbal 30. Thus, when the mobile shuttle 330 is positioned adjacent to the imaging system 303, the arms 413, 415 of the mobile shuttle 330 may be completely hidden behind the gimbal 30 when the system 300 is viewed head-on, as illustrated in FIG. 1D.

In some embodiments, a reinforcing member 417 may extend between the arms 413, 415 and may also be connected to the bridge portion 411, as shown in FIG. 1B. The reinforcing member 417 may have a curved shape that may conform to the shape of the outer circumference of the O-shaped gantry 40. The reinforcing member 417 may be offset from the rear face of the gantry 40 as shown in FIG. 4B. The reinforcing member 417 may extend radially-outwards from the outer circumference of the gantry 40 to enable the gantry 40 to tilt on the gimbal 30. The arms 413, 413, the connecting member 409 and optional reinforcing member 417 preferably do not interfere with any cables or fluid lines extending through the bore 307 of the gantry 40 (e.g., as may be required by an anesthesiologist) and may have a relatively small profile in the lateral direction (i.e., parallel to the imaging axis of the gantry 40, or in the z-axis direction), such as less than about 10 inches in lateral width (e.g., less than 8 inches in lateral width, including less than about 6 inches in lateral width). This may enable a patient 200 extending into or through the bore 307 of the gantry 40 to be easily accessed from the rear side of the gantry 40 without interference from the mobile shuttle 330.

The at least one arm 413, 415 extending from the base 401 of the mobile shuttle 330 may be off-set from the support member 350 upon which the at least one robotic arm 301 is mounted. As shown in FIGS. 1B and 1C, for example, the arms 413, 415 may be located adjacent to a face (e.g., rear face) of the gantry 40 and gimbal 30 and the support member 330 may extend above the arms 31, 33 of the gimbal 30 and over the outer circumference of the gantry 40. A lateral connector portion 419 may extend in a lateral direction (i.e., parallel to the imaging axis of the gantry 40, or in the z-axis direction) between each of the arms 413, 415 and the respective first and second ends 351, 353 of the support member 350. The lateral connector portion 419 may be a separate structure that is secured (e.g., bolted or welded) between the end of an arm 413, 415 and the respective end 351, 353 of the support member 350, as shown in FIGS. 1A-1D. Alternately, the support member 350 and arm(s) 413, 415 may be formed as a unitary structure having a bent or curved segment forming the lateral connector portion 419. As shown in FIGS. 1A-1D, the lateral connector portions 419 may have a curved profile that corresponds with an outer surface of the arms 31, 33 of the gimbal 30. Thus, when the mobile shuttle 330 is positioned adjacent to the imaging device 303, the ends of each of the arms 31, 33 of the gimbal 30 may be nested beneath the connector portions 419.

FIGS. 1A-1D schematically illustrate a support arm 421 for an optical sensor device 311 (e.g., multi-camera array) of a motion tracking system 305 mounted to the mobile shuttle 330. The support arm 421 may be mounted to the support member 350. In some embodiments, the support arm 421 may be a telescoping arm in order to adjust the length of the support arm 421. Alternately, the support arm 421 may have a fixed length. The support arm 421 may also rotate or pivot on a first joint 423 to adjust the rotational position of the optical sensor device 111. The support arm 421 may also include a second joint 425 (e.g., a ball joint) at the distal end of the arm 421 to adjust the orientation of the optical sensor device 111. The support arm 421 may include a handle 427 at the distal end of the arm 421 to enable a user to adjust the pose of the optical sensor device 111. The support arm 421 may include features that hold the optical sensor device 111 in a desired pose during a surgical procedure.

Figure 3:
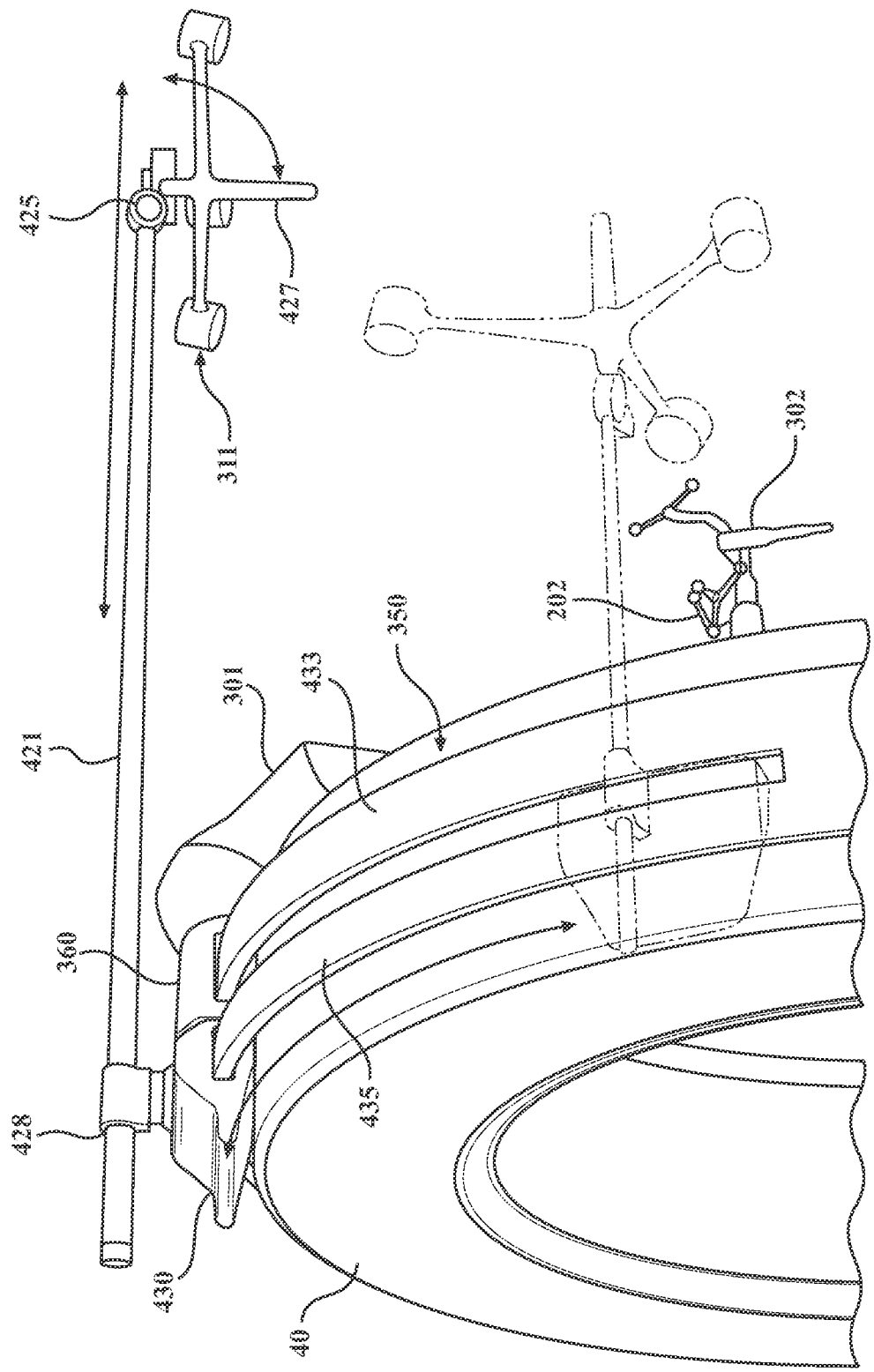
FIG. 3 illustrates a top portion of a gantry of an imaging system and a support member for mounting a robotic arm and an optical sensor device for a motion tracking system.

There are a variety of ways in which a support arm 421 for an optical sensor device 311 may be mounted to a mobile shuttle 330. In embodiments, the support arm 421 may be clamped or otherwise fastened onto the support member 350. The support arm 421 may be moved to various positions along the length of the support member 350 and fastened in place at a desired position. In some embodiments, the support arm 421 may be permanently mounted to a particular position on the support member 350. Alternately, the support arm 421 may be removably mounted (e.g., clamped onto) or non-removably mounted (e.g., bolted or welded) to the carriage 360 upon which the robotic arm 301 is mounted. In some embodiments, the support arm 421 may be mounted to a separate carriage that may be movable along the length of the support member 350 independent of the movement of the carriage 360 for the robotic arm 301. FIG. 3 illustrates an embodiment of a support member 350 for a mobile shuttle 330 that include a pair of curved support rails 423, 425 that extend parallel to one another over an outer surface (e.g., circumference) of the gantry 40 of an imaging system 303. In this embodiment, the robotic arm 301 is mounted to a first moveable carriage 360 on a first support rail 433 and the support arm 421 for the optical sensor device 311 is mounted to a second moveable carriage 430 on the second support rail 435. The two carriages 360 and 427 may be moved independently of one another, as illustrated in FIG. 3. The support arm 421 may also be slidable within an opening 428 in the second carriage 427 to adjust the displacement of the optical sensor device 311. In some embodiments, a support member 350 having a pair of support rails 433, 435 for first and second carriages 360, 430 may be directly mounted to the imaging device 303 (e.g., mounted to one or both arms 31, 33 of the gimbal 30) rather than to a separate mobile shuttle 330. In some embodiments, the robotic arm 301 may be mounted to a mobile shuttle 330 and the support arm 421 for the optical sensor device 311 may be directly mounted to the imaging device 303.

In various embodiments, a mobile shuttle 330 as shown in FIGS. 1A-1D may be transported via the wheels 403 to a position adjacent to the imaging device 303 such that the support member 350 for the at least one robotic arm 301 extends at least partially over the outer surface of the gantry 40. The arms 413, 415 and/or the connector portions 419 may be used by an operator to steer and maneuver the mobile shuttle 330 during transport. In some embodiments, the mobile shuttle 330 may be fixed in place when it is moved to a desired position. For example, the wheels 403 may be locked or may be retracted relative to the base 401 to lower the mobile shuttle 330 to the floor. In some embodiments, stabilizer elements may project from or may be extended down from the base to fix the position of the shuttle 300 on the floor. Alternately, the shuttle 330 may remain moveable with respect to the floor. In some embodiments, an attachment mechanism 439 (schematically illustrated in FIG. 1B) may be utilized to physically couple the mobile shuttle 330 to the imaging system 303. In the example shown in FIG. 1B, the attachment mechanism 439 is located on the arms 413, 413 of the mobile shuttle 330 and couples the arms 413, 413 to the arms 31, 33 of the gimbal 30 on the imaging system 303. However, one or more attachment mechanism 439 may be located on any portion of the mobile shuttle 330 (e.g., the rails 405, 407, connecting member 409, lateral connector portion 419 or support member 350) for coupling the shuttle 300 to a portion of the imaging system 303. In general, the attachment mechanism 439 may couple the mobile shuttle 330 to a portion of the imaging system 303 that moves relative to the patient 200 during an imaging scan, such as the gantry 40 or the gimbal 30. This may enable the mobile shuttle 330 and the robotic arm 301 to move with the gantry 40 and gimbal 30 during an imaging scan. The mobile shuttle 330 may also move with the entire imaging system 303 when the system 303 is transported.

The attachment mechanism 439 may be any suitable mechanism for physically coupling the mobile shuttle 330 to a portion of the imaging system 303, such as a clamp, a latch, a strap that can be secured around a portion of the imaging system 303 or a pair of mechanical stops that "capture" a portion of the imaging system 303 to enable bi-directional translation of the mobile shuttle 330 in coordination with the translation of at least a portion of the imaging system 303 relative to the patient 200.

In some embodiments, the mobile shuttle 330 may include hinged or telescoping features that may enable a user to adjust the size of the shuttle 330 or the position of the support member 350 which may allow the shuttle 330 to fit over different imaging devices, or to reduce the size of the shuttle 350 for transport. In some embodiments, the mobile shuttle 330 may include a cable management system for routing cables to and from the at least one robotic arm 301 and/or the optical sensor device 311. In embodiments, one or more electrical connections for power and/or data for the at least one robotic arm 301 and/or the optical sensor device 311 may be located on or within the mobile shuttle 330 and may be routed to a single external connector or set of connectors on the shuttle 330.

Figure 2:
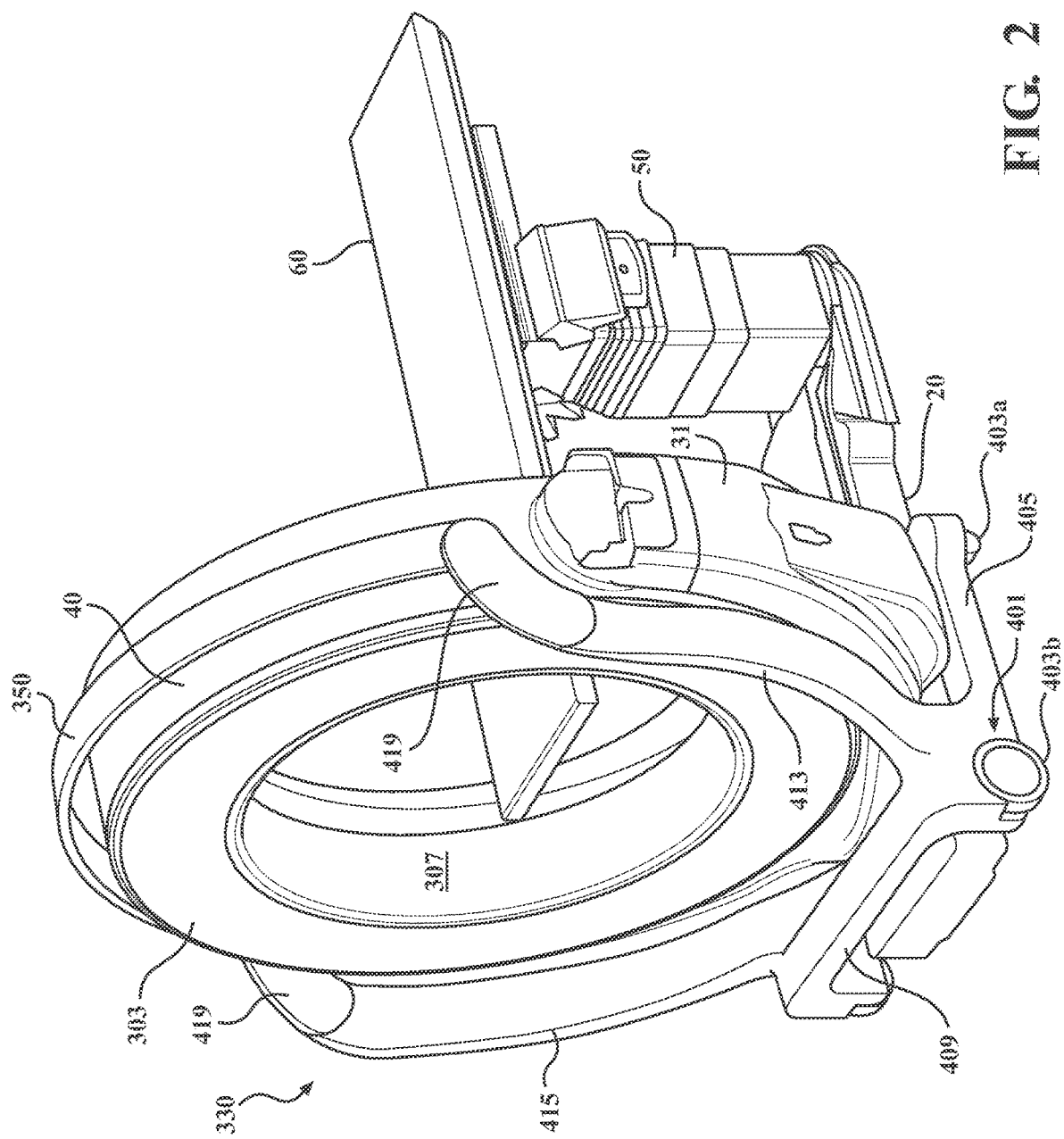
FIG. 2 illustrates a mobile shuttle for mounting at least one robotic arm according to an embodiment.

FIG. 2 is a rear perspective view of an alternative embodiment of a mobile shuttle 330 positioned adjacent to an imaging device 303. The patient support 60 in this embodiment is rotated in-line with the base 20 and extends partially into the bore 307 of the gantry 40. The mobile shuttle 330 in this embodiment is shown without a robotic arm mounted to the shuttle 330. In this embodiment, the support member 350, lateral connector portion 419 and arms 413, 415 are shown as a unitary structure. The wheels 413 in this embodiment include a set of casters 403a at a forward position on the base 401, and fixed wheels 403b at the rear of the base 401.

Figure 4A:
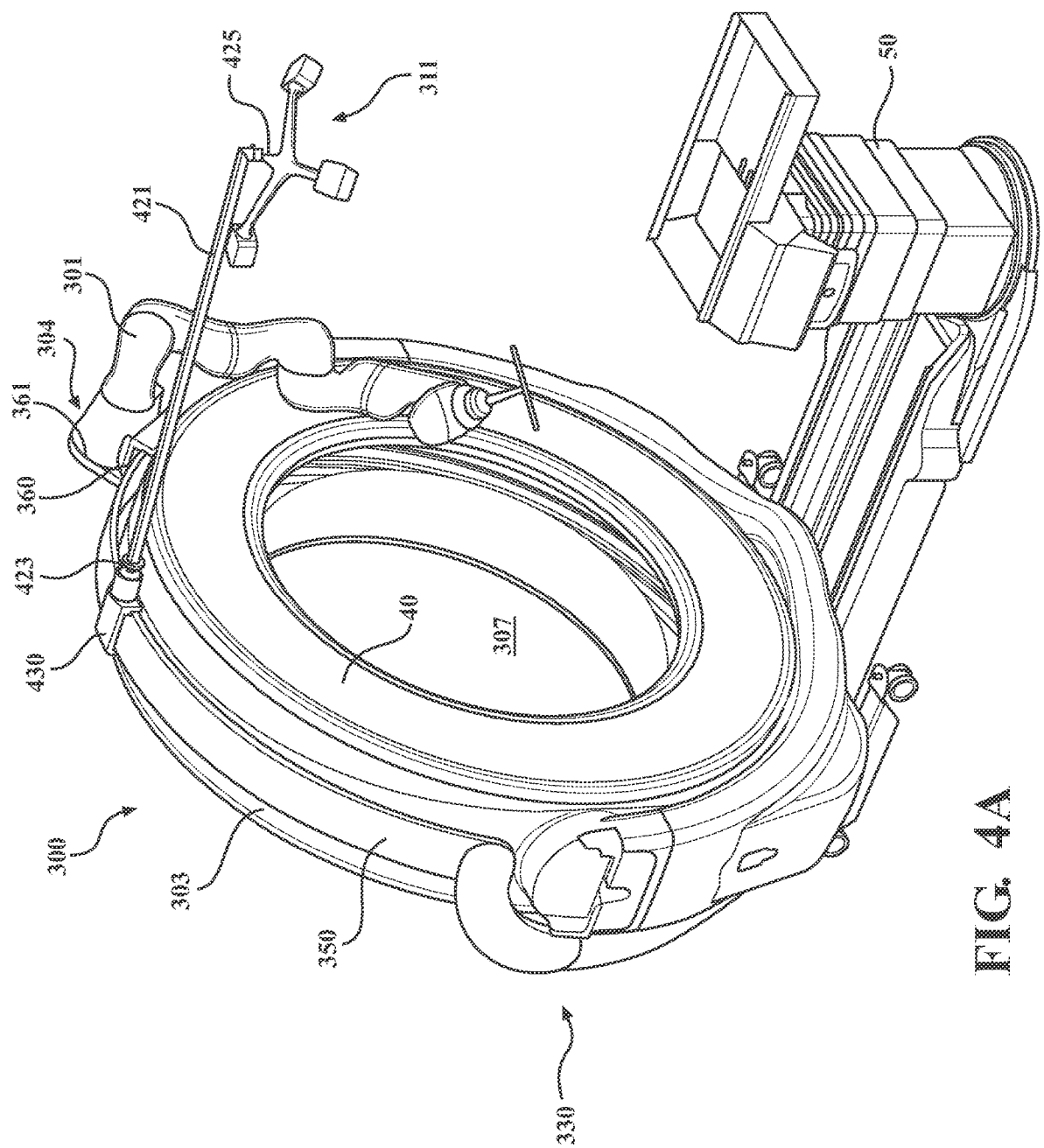
FIGS. 4A-4D illustrate an alternative embodiment of a mobile shuttle for a robotically-assisted surgical system.
Figure 4B:
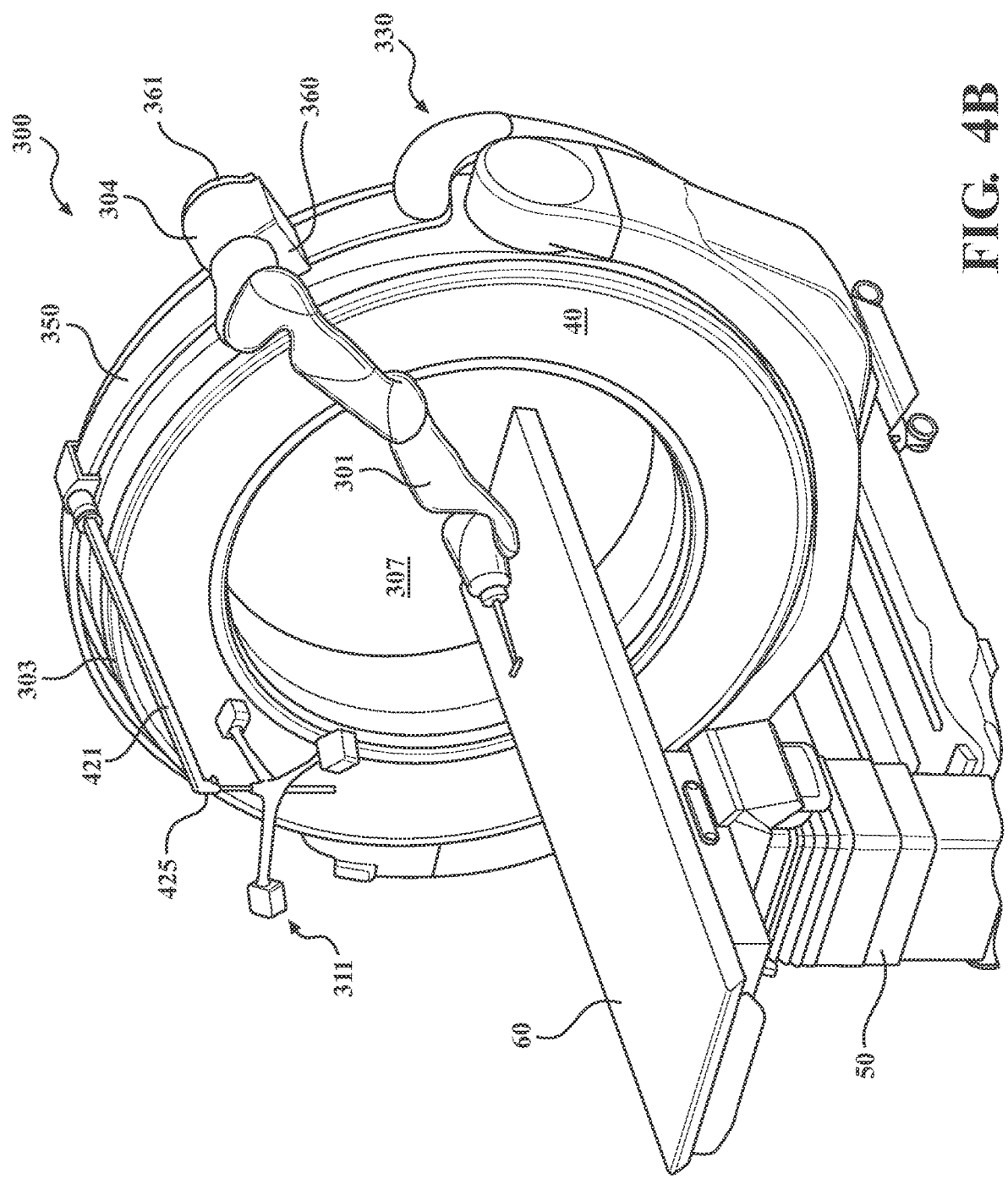
Figure 4C:
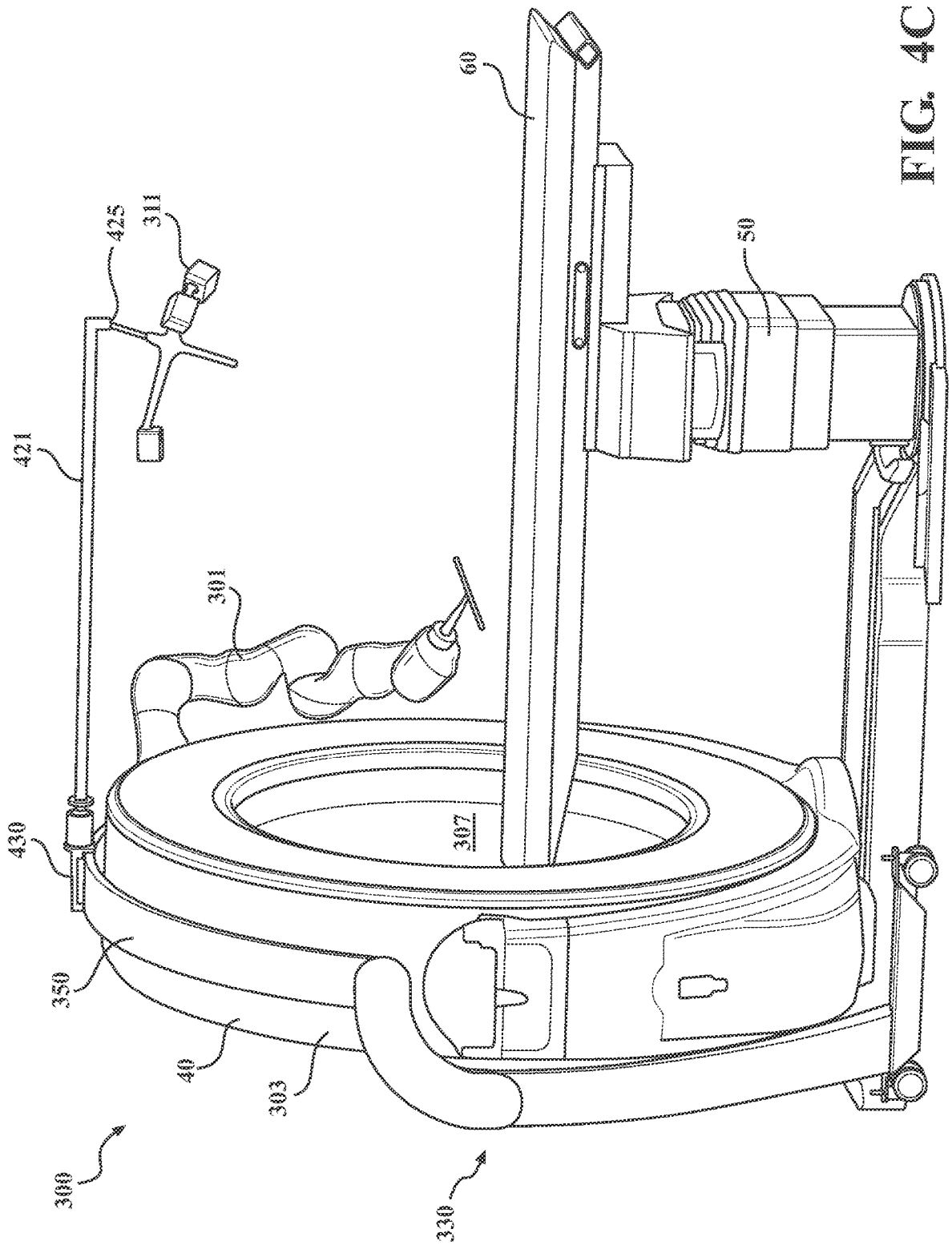
Figure 4D:
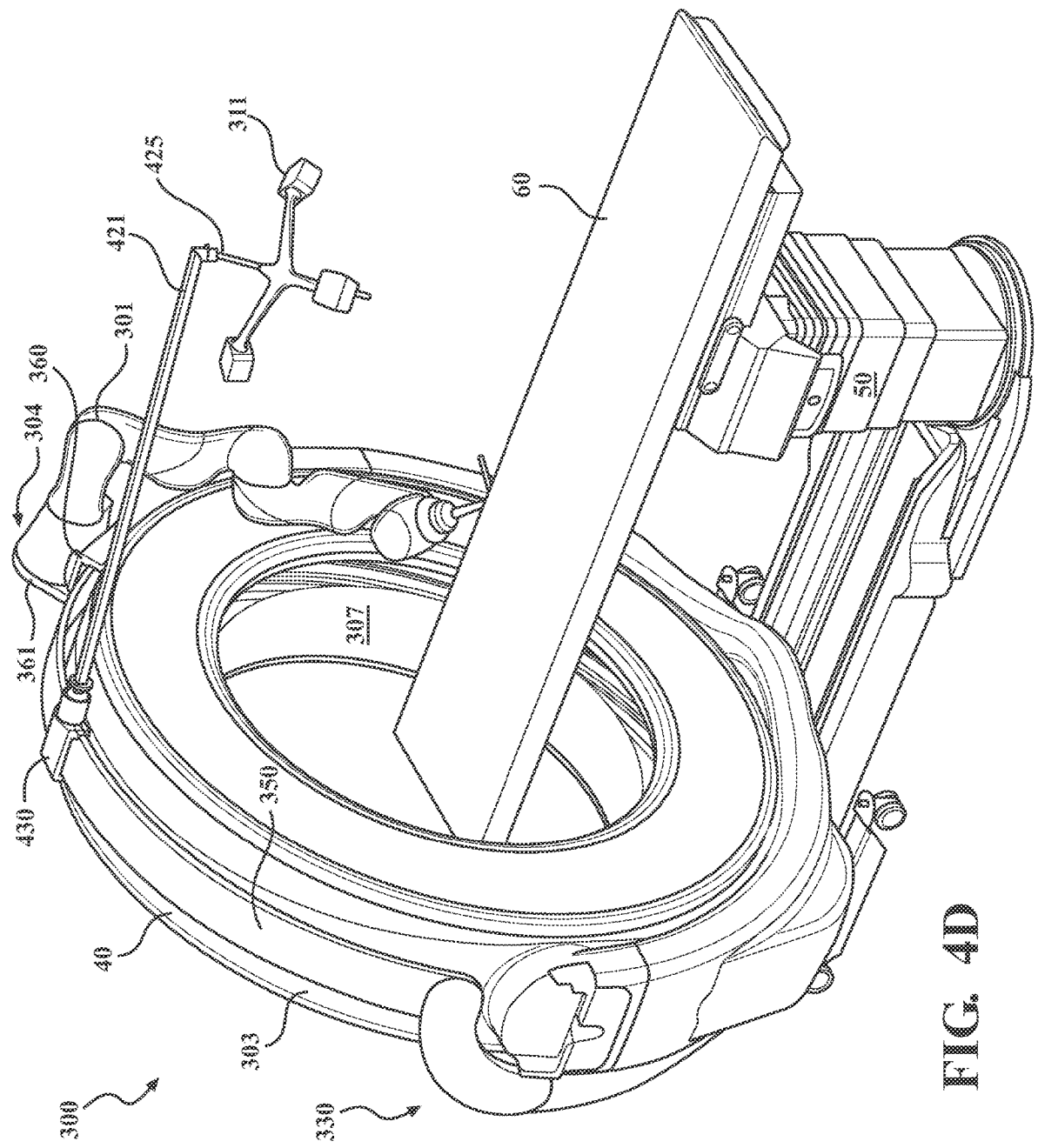

FIGS. 4A-4D illustrate an alternative embodiment of a mobile shuttle 330 positioned adjacent to an imaging device 303. FIG. 4A is a top perspective view of the mobile shuttle 330 and the imaging device 303 with the patient support 60 removed from the column 50. FIGS. 4B-4C are perspective views showing the patient support 60 attached to the column 50 and rotated in-line with the bore 307 of the gantry 40. In this embodiment, a robotic arm 301 is mounted to a first moveable carriage 360 on a support member 350 (e.g., a curved rail) of the mobile shuttle 330, and an optical sensor device 311 for a motion tracking system is mounted to a second moveable carriage 430 that is also located on the support member 350 (e.g., curved rail). In this embodiment, the first and second carriages 360, 430 may slide independently over the same support member 350 to adjust their positions relative to the patient and to one another. In addition, as is most clearly visible in FIGS. 4A, 4B and 4C, the mounting surface 361 for the base end 304 of the robotic arm 301 is angled upwards from the top of the first carriage 360. The robotic arm 301 may thus extend in a lateral direction from the mounting surface 361 over the top surfaces of the carriage 360, support member 350 and gantry 40 and may then extend down over the front face of the gantry 40 as shown in FIGS. 4A-4D. The mounting surface 361 may be at any angle with respect to the top surface of the carriage 361, such as about 90° as shown in FIGS. 4A-4D. As also shown in FIGS. 4A-4D, a support arm 421 for the optical sensor device 311 is attached to the second carriage 430. The support arm 421 in this embodiment has a fixed length. A first joint 423, which may be a rotating ball joint, enables the support arm 421 to be pivoted on the second carriage 430. The first joint 423 may have a locking mechanism to lock the joint 423 in place. A second joint 425 at the distal end of the arm 421, which may also be a rotating ball joint, may enable adjustments to the orientation of the optical sensor device 111. The second joint 425 may also have a locking mechanism to lock the joint 423 in place. In this embodiment, the second carriage 430 may be manually moved to a desired position on the support member 350 and a clamping mechanism may enable the second carriage 430 to be fixed in place. Alternately, the second carriage 430 may be driven on the support member 350 by an active drive system.

Various embodiments of a mobile shuttle 330 may enable one or more robotic arms 301 to be moved to any position along a support member 350, such as a curved rail. Since the base end 304 of the robotic arm 301 may be mounted above the gantry 40, the robotic arm 301 can be easily moved out of the way of the surgical area, such as by raising the entire arm 301 above the patient 200. When the patient table 60 is in a position as shown in FIGS. 1A-1D, the base end 304 of the robotic arm 301 can be moved on the support member 350 to any position along length of patient 200 so that the robotic arm 301 may approach the patient from the side of the patient 200 or at an oblique angle relative to the patient axis. When the table 60 is rotated in-line with gantry 40 as shown in FIG. 2, the robotic arm 301 can approach patient along the patient axis or in a direction that is generally parallel to the patient axis. The robotic arm 301 may also be moved down towards the ends 351, 353 of the support member 350, which may enable the robotic arm 301 to approach the patient 200 in a lateral direction. Various embodiments may enable a robotic arm 301 to easily access a patient 200 that is located within or extends through the bore 307 of the gantry 40 of the imaging system 303. In various configurations, the robotic arm 301 may extend down from above the patient 200, which may conserve valuable space in the surgical theater.

Various embodiments of a mobile shuttle 330 have been described for mounting at least one robotic arm 301 in close proximity to an imaging device 303 having a generally O-shaped gantry 40, where the gantry 40 is supported above a base 20 by a generally U-shaped gimbal 30. However, it will be understood that a mobile shuttle 330 may be used for mounting one or more robotic arms 301 proximate to other types of imaging systems, such as an x-ray imaging system having an O-shaped imaging gantry mounted to a mobile support structure in a cantilevered fashion as well as other x-ray imaging systems having imaging gantries with different geometries. In some embodiments, a mobile shuttle 330 may be used for mounting one or more robotic arms 301 proximate to an x-ray imaging system having a C-arm type gantry, or to imaging devices utilizing different imaging modalities (e.g., MRI, PET, SPECT, ultrasound, etc.). In general, a mobile shuttle 330 according to various embodiments may include a mobile base that may be moved adjacent to an imaging device such that a support element supported by the mobile base extends at least partially over a gantry of the imaging system, and a base end of at least one robotic arm is mounted to the support element. Further, in addition to imaging systems used diagnostic imaging of a human patient, a mobile shuttle 330 in various embodiments may also be configured for mounting at least one robotic arm 301 proximate to an imaging system used for veterinary imaging or for industrial/commercial applications, such as part inspection and assembly.

Figure 5:
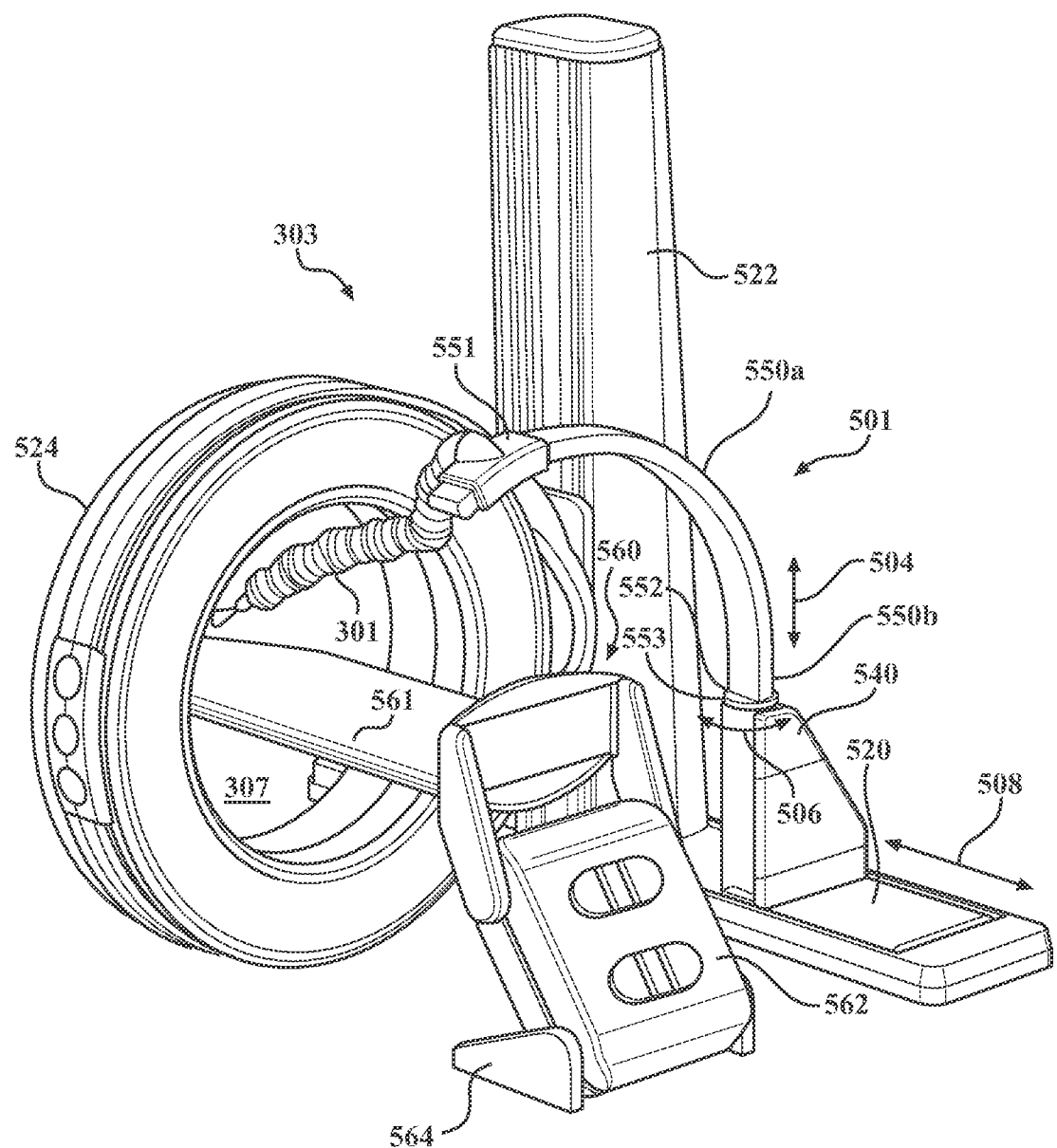
FIG. 5 illustrates an embodiment of a mounting apparatus for a robotically-assisted surgical system mounted on an imaging system.

FIG. 5 illustrates an embodiment of a mounting apparatus 501 for a robotic arm 301 located on a portion of an imaging system 303. The robotic arm 301 may be similar or identical to the robotic arm 301 described above. The imaging system 303 in this embodiment includes an elongated base 520 that may be fixed to a weight-bearing surface (e.g., the floor), a support post 522 that extends vertically from the base 520 and an imaging gantry 524 that is attached to the support post 522 on one side such that the gantry 524 is supported in a cantilevered manner. A patient table 560 is located adjacent to the imaging system 303, and includes a bed portion 561 for supporting a patient during an imaging scan. In some embodiments, the bed portion 561 may pivot with respect to a linkage member 562, and the linkage member 562 may pivot with respect to a base portion 563 that is fixed to the floor to enable the bed portion 561 to be raised and lowered with respect to the floor and/or to change the tilt angle of the bed portion 561 with respect to the floor. The gantry 524 may be translatable in a vertical direction along the length of the support post 522 to raise and lower the gantry 524 relative to the floor, and the gantry 524 may also be rotatable with respect to the support post 522 to modify the tilt axis of the gantry 524. In embodiments, the support post 522 and gantry 524 may be translatable in a horizontal direction along the length of the base 520 to perform an imaging scan (e.g., a helical x-ray CT scan) of a patient lying on the patient table 560.

The mounting apparatus 501 for the robotic arm 301 may include a base portion 540 that is located on the base 520 of the imaging system 303. A support member 550 may extend from the base portion 540 over the top surface of the patient table 560 and at least partially above a patient supported thereon. The robotic arm 301 may be mounted to the support member 550. As shown in FIG. 5, a bracket member 551 may be located on the support member 550, and the robotic arm 301 may be mounted to the bracket member 551. In some embodiments, the bracket member 551 may be slideable along the length of the support member 550 to adjust the position of the robotic arm 301.

The support member 550 may include a curved portion 550a (e.g., curved rail) that extends over the patient table 560 and a straight portion 550b proximate to the base portion 540. In embodiments, the straight portion 550b may extend and retract into a housing in the base portion 540 so that the support member 550 may be raised and lowered in the direction of arrow 504. The support member 550 may be raised and lowered in conjunction with the raising and lowering of the patient table 560 and/or the gantry 524 of the imaging system 100. The support member 550 may be raised and lowered manually and/or using a motorized system that may be located within the base portion 540. The support member 550 may be fixed in place when it is raised or lowered to a desired height.

In addition to a curved support member 550, in some embodiments the support member 550 may comprise one or more straight segments (e.g., rail segments), where at least a portion of the support member 550 may extend over the top surface of the patient table 560 and at least partially above a patient supported thereon.

In embodiments, the support member 550 may also be rotatable with respect to the base portion 540 in the direction of arrow 506, as shown in FIG. 5. For example, the straight portion 550b of the support member 550 may extend through a cover 552 that may rotate with respect to the base portion 540 on a rotary bearing 553. This may enable the support member 550 to be rotated out of the way of the patient table 560 and patient when the robotic arm 301 is not needed.

In embodiments, the base portion 540 may be weighted to provide stability to the robotic arm 301 attached to the support member 550. The base portion 540 may enclose electronic circuitry and/or processor(s) used to control the operation of the robotic arm 301. One or more connections for power and/or data may extend over or through the support member 550 and may connect the robotic arm 301 to a control system (e.g., computing device) and/or a power supply that may be located in the base portion 540. The base portion 540 may be permanently fixed to the base 520 of the imaging system 100 or may be removably mounted to the base 520. For example, the mounting apparatus 501 may be moved using a mobile cart or shuttle (not illustrated) and may be lifted from the mobile cart/shuttle and placed onto the base 520 of the imaging system 303. In embodiments, the base portion 540 may be clamped or otherwise fixed in place on the base 520.

In some embodiments, the mounting apparatus 501 may be moveable along the length of the base 520. For example, the base portion 540 of the mounting apparatus 501 may include one or more bearing elements (e.g., rollers or sliders) that engage with a bearing surface on the base 520 of the imaging system 303 and may enable the mounting apparatus to translate along the length of the base 520 in the direction of arrow 508. A drive mechanism may be mounted inside or beneath the base portion 540 to drive the translation of the mounting apparatus 501 along the base 520. In some embodiments, the mounting apparatus 501 may not include a drive system for translating the mounting apparatus 501. The base portion 540 of the mounting apparatus 501 may be mechanically coupled to the support post 522 of the imaging system 303, such as via one or more rigid spacers (not illustrated) that may extend along the length of the base 520. The spacer(s) may enable the separation distance between the mounting apparatus 501 and the support post 522 to be adjusted. The translation of the support post 522 along the base 520 may drive the translation of the mounting apparatus 501 to which it is attached.

A system such as shown in FIG. 5 may be utilized for performing a variety of different diagnostic and treatment methods. In some embodiments, the system may be used for robot-assisted interventional radiology procedures. For example, the end effector of the robotic arm 301 may include or may hold an invasive surgical tool, such as a biopsy needle, that may be inserted into the body of a patient on the patient table 560. The imaging system 303 may obtain images of the patient (e.g., CT scans, such as CT fluoroscopic scans) that may be used to guide the insertion of and confirm the position of an invasive tool or instrument. As shown in FIG. 5, in some embodiments the robotic arm 301 may be extended to a position that is at least partially within the bore 307 of the imaging gantry 524.

In embodiments, a system as shown in FIG. 5 may be used for an image-guided surgical procedure, and may include a sensing device (e.g., a camera array) for tracking the relative positions and orientations of various objects within the surgical space. A motion tracking device (e.g., camera array) may be mounted to the mounting apparatus 501, such as on the support member 550 (e.g., curved rail), similar to the embodiments of FIGS. 1A-1C, 3 and 4A-4D described above. Alternately, the motion tracking device may be mounted to the imaging system 303, the patient table 360 or to a separate cart.

Figure 6A:
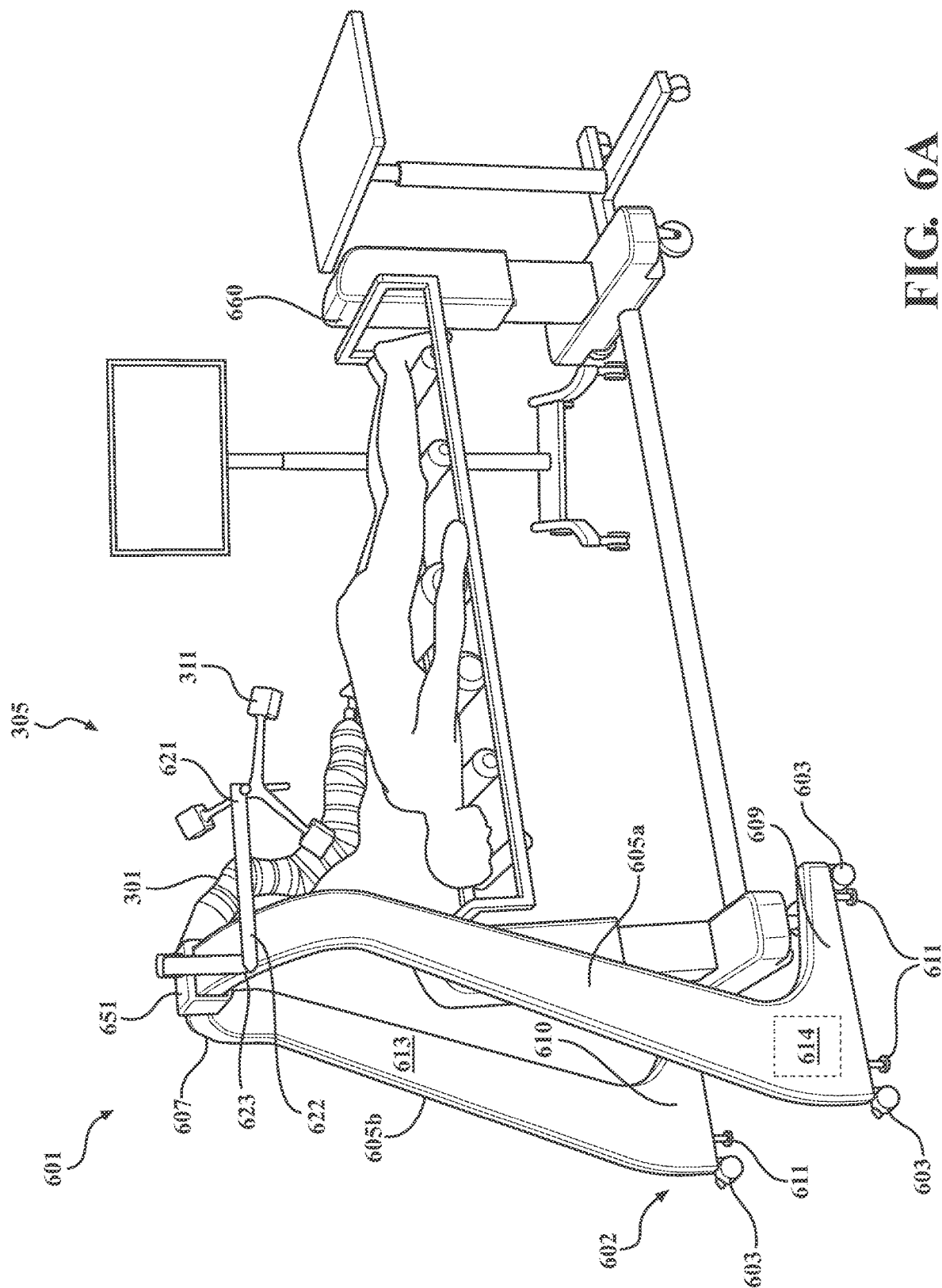
FIGS. 6A-6B illustrate a further embodiment of a mobile mounting apparatus for a robotic arm used for robotically assisted surgery.
Figure 6B:
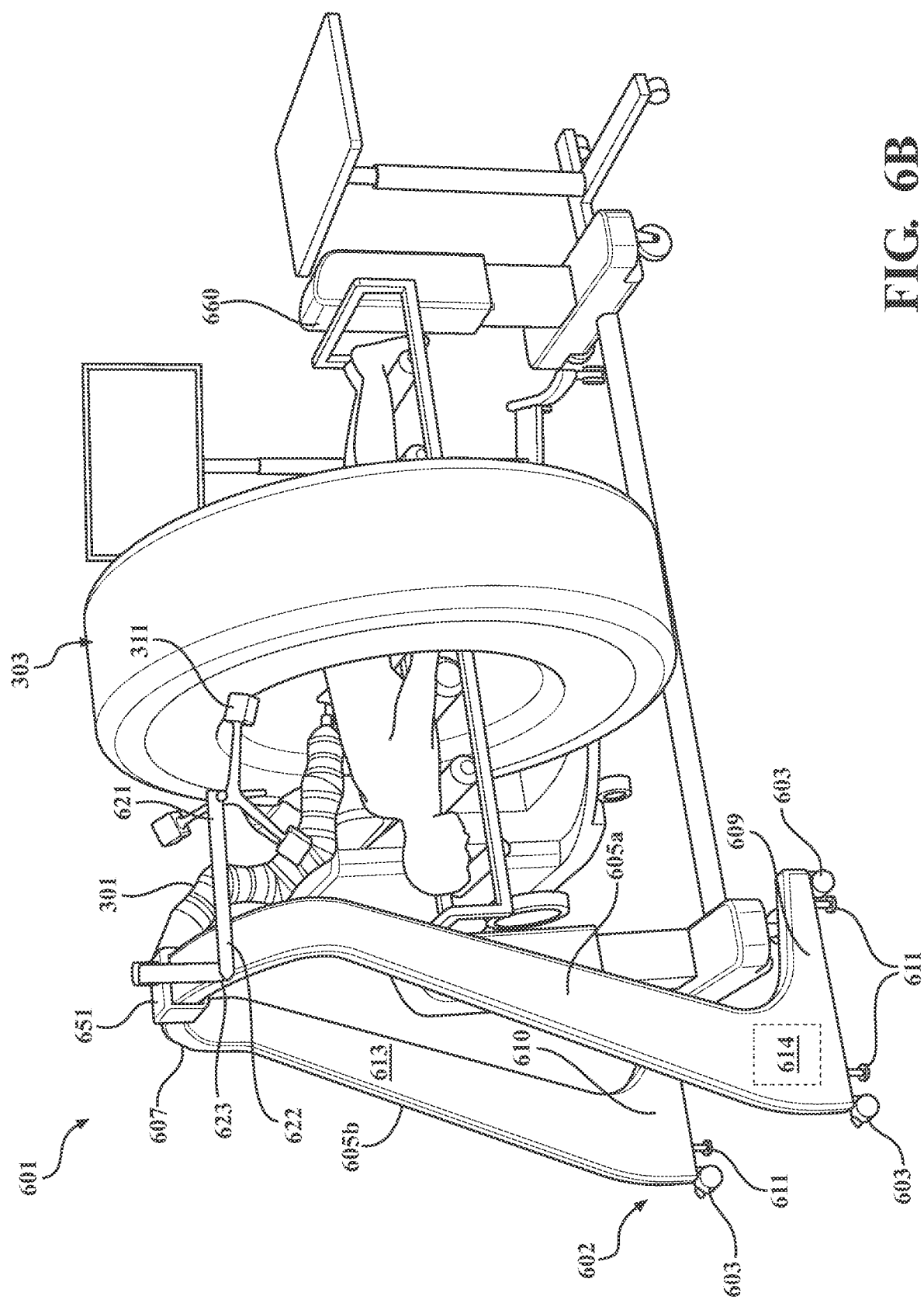

FIGS. 6A-6B illustrate a further embodiment of a mounting apparatus 601 for a robotic arm 301 used for robotically assisted surgery. The mounting apparatus 601 may be a mobile apparatus (i.e., a cart or shuttle) that may be used to position the arm 301 for performing a surgical procedure as well as for transport and/or storage of the robotic arm 301. The mounting apparatus 601 in this embodiment includes a base portion 602 having a plurality of wheels 603, a pair of support arms 605a, 605b extending upwards from the base portion 602, and a support member 607 extending between the support arms 605a, 605b. At least one robotic arm 301 may be attached to the support member 607. The support member 607 may be a curved rail to which the robotic arm 301 is attached. The mounting apparatus 601 may be similar to a mobile shuttle 330 such as described above with reference to FIGS. 1A-4D, although the support member 607 in this embodiment does not extend over an outer surface of a gantry of an imaging system. The mounting apparatus 601 may have a smaller profile (e.g., height and/or width dimension) than the mobile shuttle 330 as shown in FIGS. 1A-4D.

The mounting apparatus 601 may be positioned adjacent to a patient table 660. The patient table 660 may be an operating table, such as a Jackson table as shown in FIGS. 6A and 6B. The mounting apparatus 601 and the robotic arm 301 may be utilized with or without an imaging device located in the operating theater. FIG. 6A illustrates the mounting apparatus 601 and robotic arm 301 used to perform robotically-assisted image guided surgery without an intra-operative imaging system. FIG. 6B illustrates the mounting apparatus 601 and robotic arm 301 used to perform robotically-assisted image guided surgery with an imaging system 303 (e.g., an O-arm® system, a C-arm system, etc.) located in the operating theater. The imaging system 303 may approach the patient from the side of the patient table 660 to obtain images of the patient. The mounting apparatus 601 may be positioned adjacent to an end of the patient table 660 such that the robotic arm 301 may extend from the mounting apparatus 601 along the length of the patient table 660 to the surgical area.

The base portion 602 may include a pair of spaced-apart foot sections 609, 610 extending parallel to one another. Wheels 603 (e.g., casters) may be located at the front and rear of each foot section 609, 610 to enable transport of the mounting apparatus 601. One or more stabilizers 611 may be extended from the bottom of each foot section 609, 610 to contact the floor and maintain the mounting apparatus 601 in a fixed location. The stabilizers 612 may be extended from and retracted into the respective foot sections 609, 610 manually (e.g., via a lever or foot pedal, for example). In some embodiments, a motorized system located in the foot sections 609, 610 may drive the extension and retraction of the stabilizers. Alternately or in addition, the wheels 603 may be retracted into the foot sections 609, 610 to lower the mounting apparatus 601 to the floor at a desired location.

The support arms 605a, 605b may extend from the rear of the base portion 602 and may extend upwards at an angle towards the front of the mounting apparatus 601. An open region 613 may be defined between the foot sections 609, 610, the support arms 605a, 605b and the support member 607. In embodiments, the foot sections 609, 610 and support arms 605a, 605b on either side of the mounting apparatus 601 may not be connected to one another except at the top of the mounting apparatus 601 (e.g., via the support member 607). This may enable the mounting apparatus 601 to be positioned over a patient table 660 such that the mounting apparatus 601 may at least partially straddle the patient table 660, such as shown in FIGS. 6A and 6B. The open region 613 may be designed to accommodate a wide variety of different types of patient tables in a "straddle" configuration. The open region 613 may also accommodate other devices within the operating theater, such as an anesthesia machine and/or a Mayo stand. In embodiments, the open region 613 may have a width of at least about 32 inches and a height of at least about 50 inches.

The foot sections 609, 610 and/or the support arms 605a, 605b may be weighted to provide stability to the robotic arm 301 attached to the support member 607. One or more housings may be formed in foot section(s) 609, 610 and/or support arm(s) 605a, 605b for enclosing electronic circuitry and/or processor(s) used to control the operation of the robotic arm 301 and/or for performing image guided surgery/surgical navigation. One or more connections for power and/or data may extend over or through the support member 607 and along one or both support arms 605a, 605b and may connect the robotic arm 301 to a control system 614 (e.g., computing device) and/or a power supply located in the mounting apparatus 601.

As shown in FIGS. 6A-6B, a bracket member 651 may be located on the support member 607, and the robotic arm 301 may be mounted to the bracket member 651. In some embodiments, the bracket member 651 may be slideable along the length of the support member 607 to adjust the position of the robotic arm 301.

A support arm 621 for an optical sensor device 311 (e.g., multi-camera array) of a motion tracking system 305 may be located on the mounting apparatus 601. The support arm 621 may be mounted to the support member 607, and may be attached to the bracket member 651 as shown in FIGS. 6A-6B. In this embodiment, the support arm 621 incudes a plurality (e.g., two) rigid segments 622 connected by joint(s) 623 (e.g., ball joints). The user may adjust the position and orientation of the optical sensor device 111 by articulating the rigid segments 622 on the joints 623. The support arm 621 may include features that hold the optical sensor device 311 in a desired pose during a surgical procedure. The support arm 621 may also be folded into compact configuration for ease of transport of the mounting apparatus 601.

Figure 7:
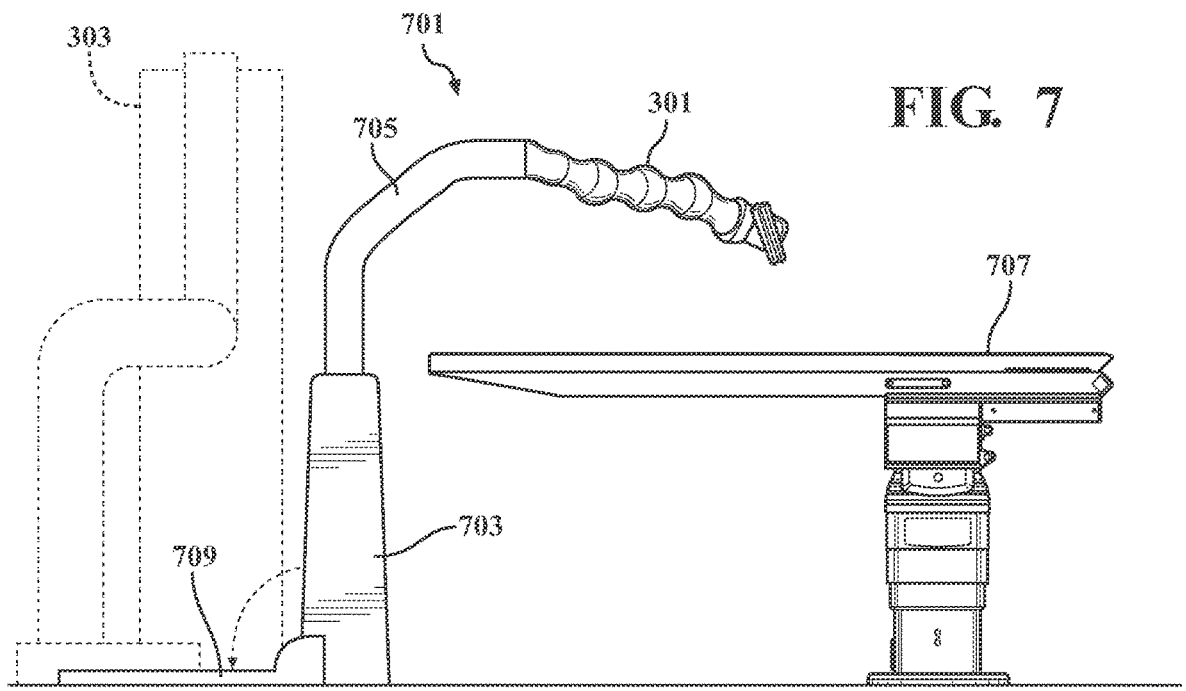
FIG. 7 illustrates a further embodiment of a mounting apparatus for a robotic arm having a selectively deployable anchoring apparatus.

FIG. 7 illustrates a further embodiment of a mounting apparatus 701 for a robotic arm 301 used for robotically assisted surgery. The mounting apparatus 701 may be a mobile apparatus that may be used to position the arm 301 for performing a surgical procedure as well as for transport and/or storage of the robotic arm 301. The mounting apparatus 701 may include a base 703 and a support arm 705 extending from the base 703, where the robotic arm 301 may be secured to the support arm 705. FIG. 7 illustrates the mounting apparatus 701 located at an end of a patient table 707 such that the robotic arm 301 may extend from the mounting apparatus 701 to a patient located on the patient table 707. An optical sensor device (e.g., multi-camera array) of a motion tracking system may also be attached to the mounting apparatus 701, as described above. A power supply and other electrical components (e.g., computer(s)) may be housed within the base 703 of the mounting apparatus 701. The mounting apparatus 701 may be a wheeled cart that includes wheels on the base 703 to enable the mounting apparatus 701 to be moved across the floor. Alternately or in addition, a separate shuttle device (not illustrated) may be utilized to transport the mounting apparatus 701 to a desired location and leave it in a fixed position (e.g., by lowering it to the floor). The shuttle device may then be moved away from the mounting apparatus 701. After use, the shuttle device may be used to lift the mounting apparatus 701 from the floor for transport to another location.

The mounting apparatus 701 in the embodiment of FIG. 7 may be relatively small and lightweight in comparison to conventional carts for surgical robotic arms. This may enable easier transportation of the mounting apparatus 701 and robotic arm 301 and may reduce the space in the operating room occupied by the surgical robot and its support structure. In embodiments, the mounting apparatus 701 may also include an anchoring apparatus 709 that may be deployed for the purposes of providing greater stability to the mounting apparatus 701 and robotic arm 301. The anchoring apparatus 709 may comprise one or more plate-shaped elements that may be pivoted downward from the base 703 to lie flat against the floor. Weight may be provided on the top surface of the anchoring apparatus 709 to provide additional ballast and improve the stability of the mounting apparatus 701 and robotic arm 301. In one embodiment, the weight may be provided by moving a mobile imaging device 303 or another heavy item of equipment in the operating theater over the anchoring apparatus 709.

Figure 8:
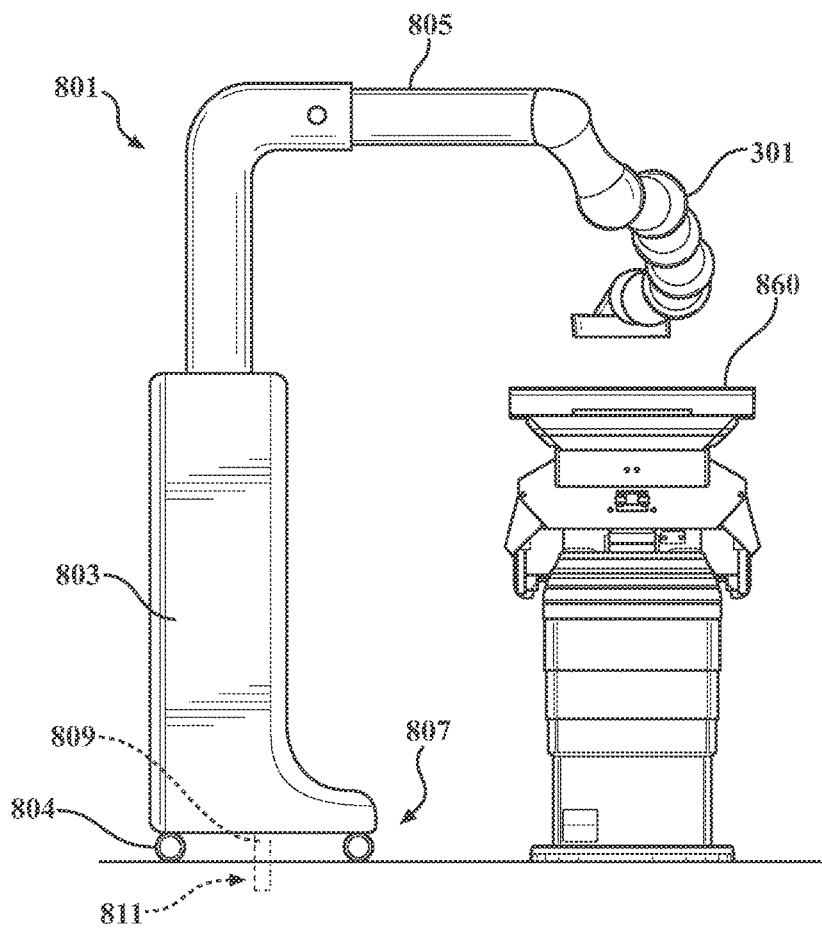
FIG. 8 illustrates a mounting apparatus for a robotic arm that includes a mobile cart and a docking system for docking the cart to a pre-installed feature in the floor.

Further embodiments include a mobile mounting apparatus for a surgical robotic arm that includes a docking system for mating with pre-installed feature(s) in the floor of the operating room. FIG. 8 illustrates a first embodiment of a mounting apparatus 801 that is a mobile cart having a base 803 with wheels 804 and a support arm 805 extending from the base 803 to which a robotic arm 301 is attached. The support arm 805 may be hinged so that the robotic arm 301 may be pivoted upwards to a raised position above a patient table 860, as shown in FIG. 8. The support arm 805 and robotic arm 301 may be pivoted downwards towards the base 803 to improve stability of the cart during transport. An optical sensor device (e.g., multi-camera array) of a motion tracking system may also be attached to the mounting apparatus 801, as described above. A power supply and other electrical components (e.g., computer(s)) may be housed within the base 803 of the mounting apparatus 801.

The docking system 807 in this embodiment includes a first docking element 809 that is extended from the bottom surface of the mounting apparatus 801 and a second docking element 811 that is located on and/or within the floor. The second docking element 811 may be a socket that is pre-installed in the floor of the operating theater. The second docking element 811 may be pre-installed in a select location of an operating room, such as adjacent to a fixed surgical table 860 or beneath overhead surgical lighting or ventilation system(s). A plurality of second docking elements 811 may be pre-installed in selected locations around the operating room. The first docking element 809 may be a threaded connector that may be extended from the bottom of the base 803 (e.g. via a motor or a foot pedal or other mechanical means) and into the second docking element 811. The second docking element 811 may have corresponding threads which engage with the threads of the first docking element 809 to mechanically couple the first and second docking elements 809, 811. In embodiments, once the docking system 807 is engaged, the first docking element 809 may be retracted back towards the base 803 of the mounting apparatus 801 to take up any play between the first and second docking elements 809, 811 and provide increased stability to the mounting apparatus 801. In some embodiments, the wheels 804 of the mounting apparatus 801 may retract into the base 804 in coordination with the extension of the first docking element 809 so that the mounting apparatus 801 may be lowered to the floor as the docking system 807 is engaged.

In embodiments, the second docking element 811 may be countersunk to facilitate engagement with the first docking element 809. The docking system 807 may also include additional features, such as mechanical, optical and/or electromagnetic features to ensure that the base 803 of the mounting apparatus 801 is properly aligned over the second docking element 811 before the first docking element 809 is extended. In some embodiments, the docking system 807 may include connections for power and/or data to and/or from the mounting apparatus 801.

The docking system 807 may be disengaged by actuating a release mechanism (e.g., a button, foot pedal, etc.) that causes the first docking element 809 and the second docking element 811 to disconnect from one another so as to enable the mounting apparatus 801 to be transported and/or re-positioned. In preferred embodiments, when the docking system 807 is disengaged, the second docking element 811 may be substantially flush with the floor surface and does not interfere with medical personnel or other equipment within the operating room.

Although the embodiment of FIG. 8 illustrates a docking mechanism 807 having a connector that extends from the mounting apparatus 801 to engage with a socket in the floor, it will be understood that the docking mechanism 807 may include a connector that extends from the floor to engage with the mounting apparatus 801.

Figure 9:
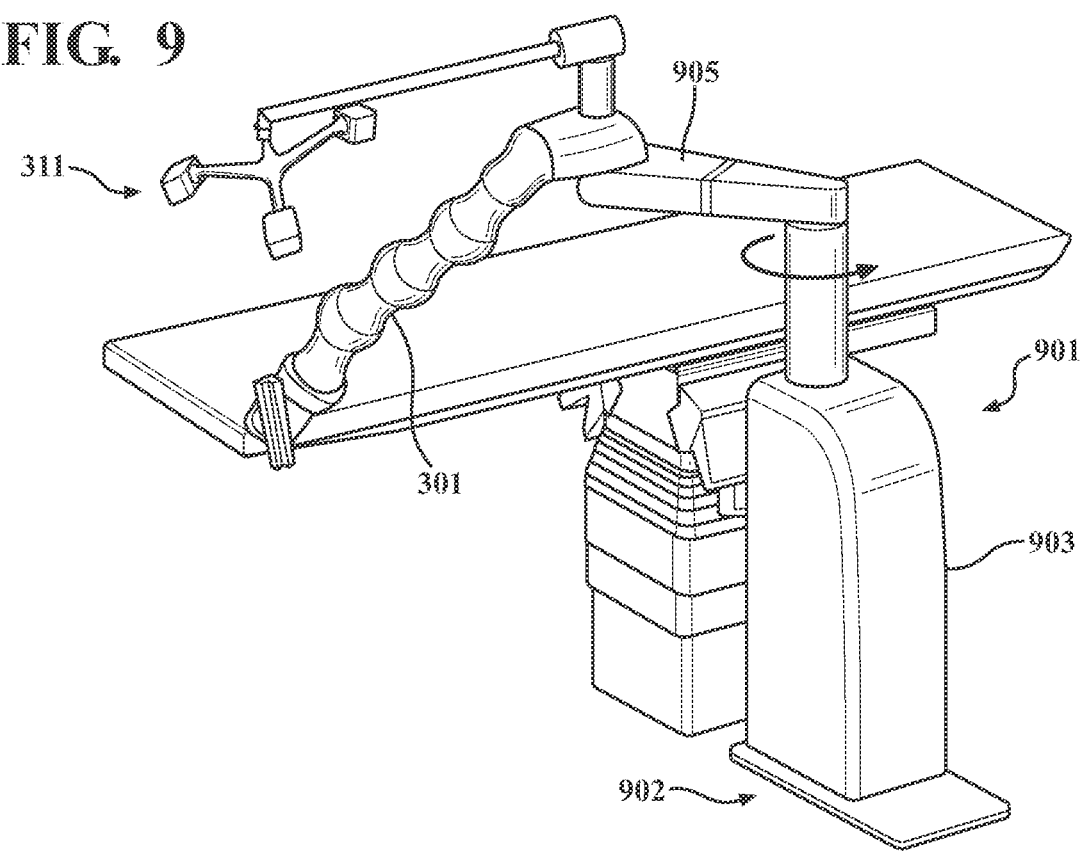
FIG. 9 illustrates another embodiment of a mobile mounting apparatus for a robotic arm that includes a docking system for docking with pre-installed features in the floor.

FIG. 9 illustrates an alternative embodiment of a mobile mounting apparatus for a surgical robotic arm that docks with pre-installed feature(s) in the operating room floor. In this embodiment, the mounting apparatus 901 may be moved using a separate shuttle device (not illustrated). The mounting apparatus 901 may be lowered onto or slid into a floor mount 902 that may be pre-installed in the floor of the operating room. The mounting apparatus 901 and/or floor mount 902 may have mating features to facilitate alignment and a locking mechanism that engages to lock the mounting apparatus 901 into position on the floor.

The mounting apparatus 901 in this embodiment includes a base 903 and a boom arm 905 that is able to swivel with respect to the base 903, as shown in FIG. 9. A robotic arm 301 and an optical sensor device 311 of a motion tracking system may be attached to the boom arm 905. In some embodiments, the height of the boom arm 905 with respect to the base 903 may be adjustable.

Figure 10:
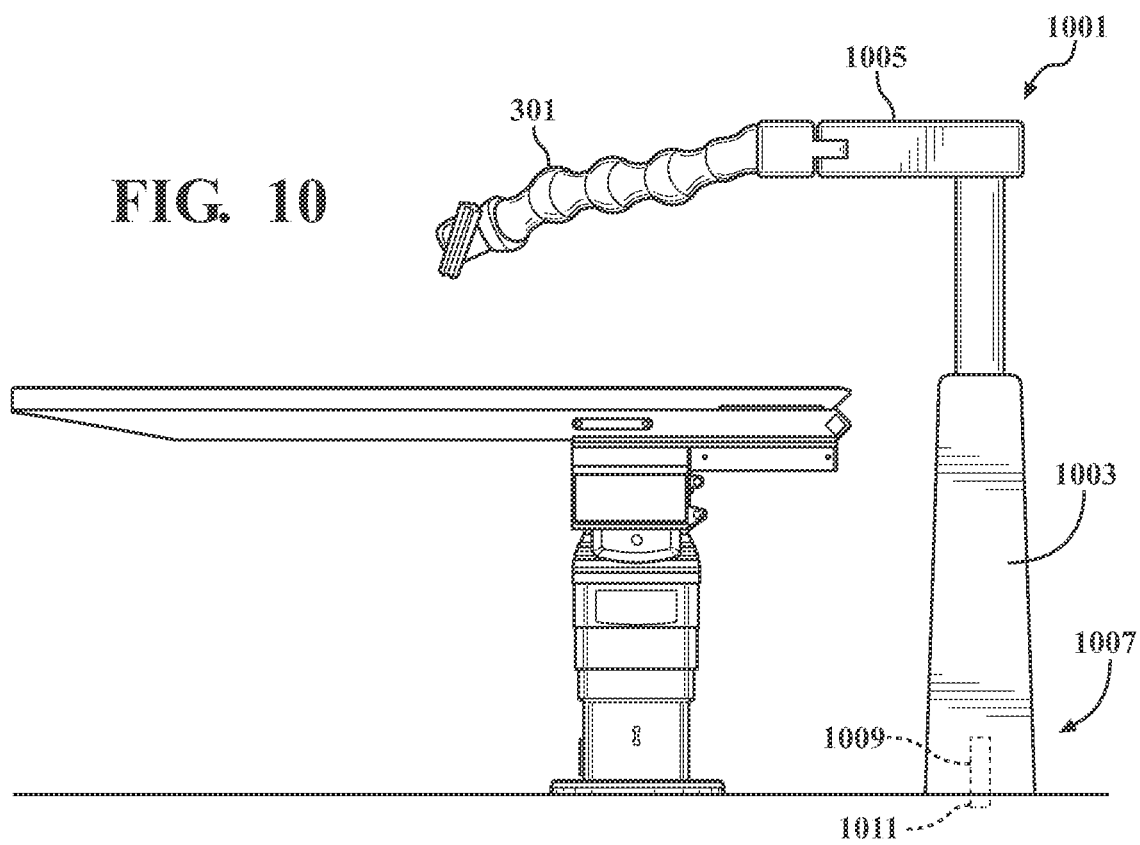
FIG. 10 illustrates yet another embodiment of a mobile mounting apparatus for a robotic arm that includes a docking system for docking with pre-installed features in the floor.

FIG. 10 illustrates a further embodiment of a mounting apparatus 1001 for a robotic arm that includes a base 1003 and a support arm 1005 extending from the base 803 to which a robotic arm 301 is attached. An optical sensor device (e.g., multi-camera array) of a motion tracking system may also be attached to the mounting apparatus 1001, as described above. A power supply and other electrical components (e.g., computer(s)) may be housed within the base 1003 of the mounting apparatus 1001.

The mounting apparatus 1001 of FIG. 10 may be similar to the mounting apparatus 801 described above with reference to FIG. 8. However, the mounting apparatus 1001 of FIG. 10 is not a wheeled cart and may be moved using a separate shuttle device (not illustrated). In addition, the mounting apparatus 1001 may be positioned adjacent to an end of a patient table. The mounting apparatus 1001 of FIG. 10 may include a docking mechanism 1007 that includes a first docking element 1009 (e.g., a threaded connector) that engages with a second docking element 1011 (e.g., socket) that is located on and/or within the floor to secure the mounting apparatus 1001 to the floor.

In some embodiments, multiple mounting apparatuses 801, 901, 1001 as described above may be docked with pre-installed docking features located at various locations in the operating room floor. Various items used during surgery, such as robotic arm(s), surgical instrument(s), instrument tray(s), camera(s), light source(s), monitor screen(s), etc., may be mounted to the mounting apparatuses 801, 901, 1001. In embodiments, multiple mounting apparatuses 801, 901, 1001 may be bridged by one or more spanning members (e.g., cross-bar(s), truss(es), etc.) that may extend over or adjacent to the surgical area, and one or more items, such as robotic arm(s), surgical instrument(s), instrument tray(s), camera(s), lighting, monitor screen(s), etc., may be suspended from a spanning member.

Further embodiments include a table mount for a surgical robotic arm. A table mount approach may minimize the size and footprint of the mounting apparatus used to mount a surgical robotic arm while enabling the robotic arm to be located in an advantageous position for performing robotically-assisted surgery. For example, a robotic arm mounted to the surgical table may have a closer physical connection and relationship to the patient, so that the robotic arm may better follow or accommodate motion of the patient. A table mount according to various embodiments may enable the robotic arm to be mounted along the edge of the patient table (i.e., along the side of the patient), at an end of the table (i.e., at the head or foot of the patient), and/or above the patient, as described in further detail below. In some embodiments, a table mount may be movable with respect to the patient table (e.g., slidable along the length of the patient table) to adjust the position of the robotic arm on the table.

FIGS. 11A-11E illustrate a first embodiment of a table mount 1101 for mounting at least one robotic arm 301 to a surgical table 1160. In this embodiment, the table mount 1101 may be used to mount a robotic arm 301 to a side 1102 of the table 1160 and/or to an end 1104 of the table 1160. It will be understood that in some embodiments, a table mount 1101 may be configured to mount a robotic arm 301 only to the side 1102 or to the end 1104 of the table 1160.

Figure 11A:
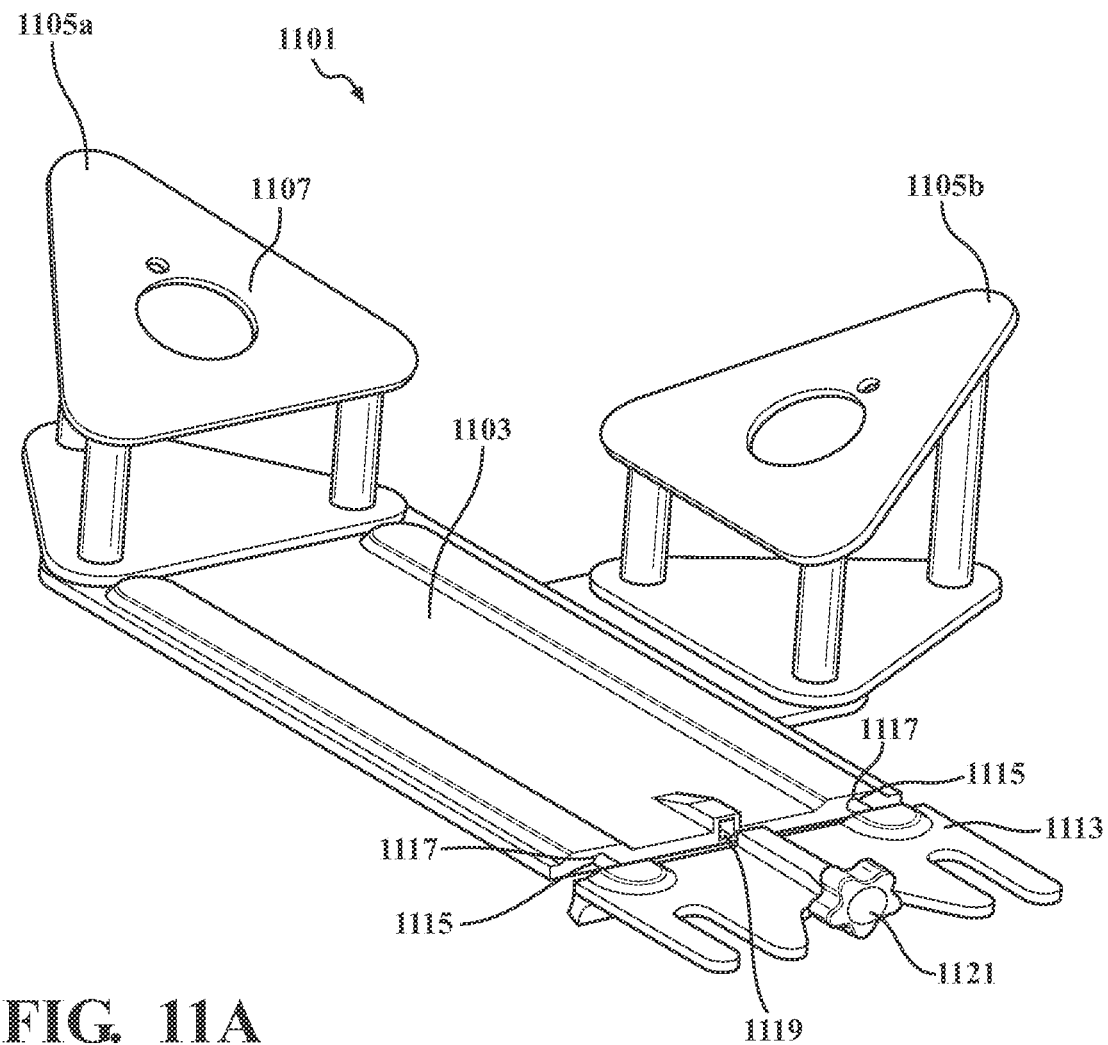

As shown in FIG. 11A, the table mount 1101 may include a generally flat plate member 1103 that may be placed on a surgical tabletop. One or more raised platforms 1105a, 1105b may extend from a periphery of the plate member 1103. The raised platforms 1105a, 1105b may be may be cantilevered from the side 1102 or end 1104 of the surgical table 1160. The raised platforms 1105a, 1105b may include a mounting surface 1107 for attaching a robotic arm 301, as shown in FIGS. 11B-11E. The mounting surface 1107 may optionally be angled toward the surface of the patient table 1160, as shown in FIGS. 11B-11E. In embodiments, the plate member 1103 may be placed across the width of the surgical tabletop 1108, and one or more tabletop pads 1110 may be placed over the top surface of the plate member 1103. The weight of the patient on the tabletop pad 1110 and plate member 1103 may provide additional ballast to improve the stability of the table mount 1101 and robotic arm 301.

Figure 11D:
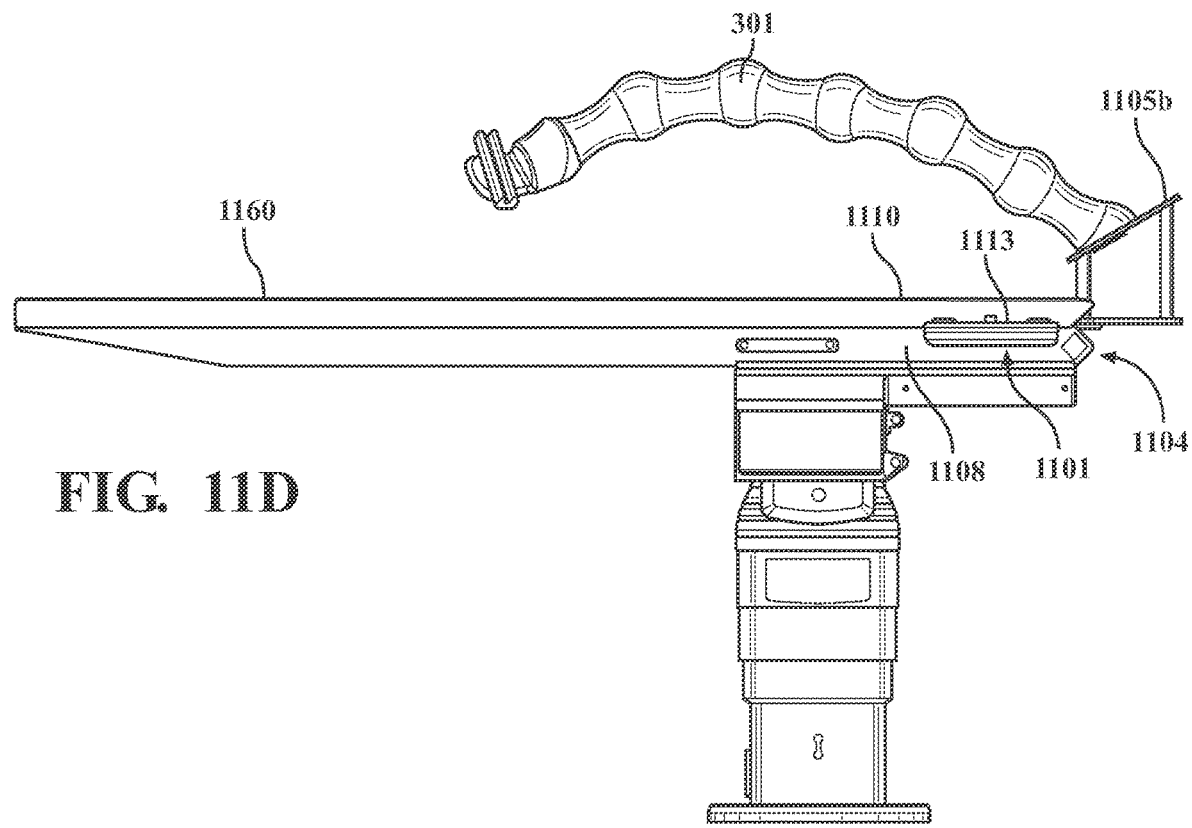
Figure 11E:
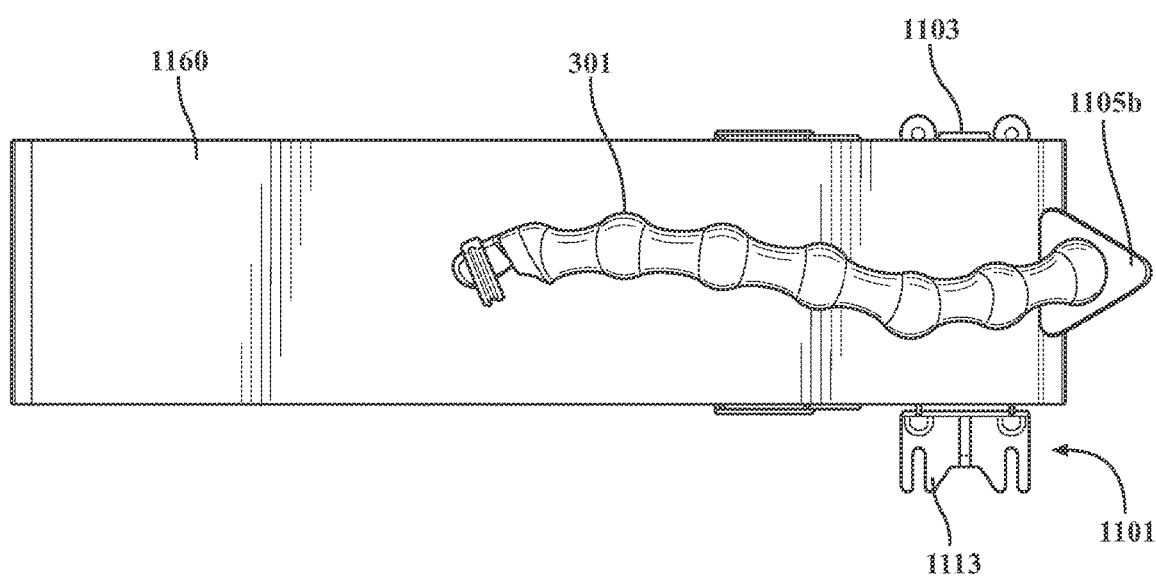

The raised platforms 1105a, 1105b may be integrally formed with or permanently mounted to the plate member 1103, or alternately, the raised platforms 1105a, 1105b may be removable from the plate member 1103. For example, as shown in FIGS. 11B and 11C, raised platform 1105b may be removed from the table mount 1101 and a robotic arm 301 may be mounted to the side 1102 of the table 1160 on raised platform 1105a. In FIGS. 11D and 11E, raised platform 1105*a* may be removed from the table mount 1101 and a robotic arm 301 may be mounted to the end 1104 of the table 1160 on raised platform 1105*b*.

The table mount 1101 may be attached to a surgical table 1160 using a clamping mechanism that may clamp the table mount 1101 across the width of the surgical table 1160. In various embodiments, the table mount 1101 may be designed for use with different types of surgical tables that may vary in terms of structural features and/or dimensions of the surgical table. Thus, a universal or semi-universal design for a table mount 1101 may be utilized. As shown in FIG. 11C, the plate member 1103 may have a first projection 1111 that extends from the bottom surface of the plate member 1103 and abuts against a structural element of the surgical table 1160 (e.g., a side surface of the table 1160, a side rail, etc.). Opposite the first projection 1111, the plate member 1103 may include a reciprocating portion 1113 that may include alignment features (e.g., rods 1115) that slide within openings 1117 in the plate member 1103. The reciprocating portion 1113 may be moved towards or away from the rest of the plate member 1103 to adjust the width of the plate member 1103. The reciprocating portion 1113 may have a second projection 1119 (see FIG. 11C) that extends from the bottom surface of the reciprocating portion 1113 and may abut against a structural element (e.g., the side surface of the table, a side rail, etc.) on the opposite side of the table 1160. The plate member 1103 may be fastened against opposite sides of the table 1160 by turning a knob 1121 (see FIG. 11A) so that a threaded connector extending through the reciprocating portion 1113 becomes engaged within a threaded opening 1119 in the plate member 1103.

In addition to mounting a robotic arm 301 as shown in FIGS. 11B-11E, a table mount 1101 as described above may be used to mount other items to a surgical table, such as surgical tools, instrument trays, cameras, monitors/displays, light sources, etc.

FIGS. 12A-12E illustrate a second embodiment of a table mount 1201 for mounting at least one robotic arm 301 to a surgical table 1160. In this embodiment, the table mount 1201 may include a bridge section 1202 that extends over the top surface of the surgical table 1160. At least one robotic arm 301 may be mounted to the bridge section 1202.

Figure 12A:
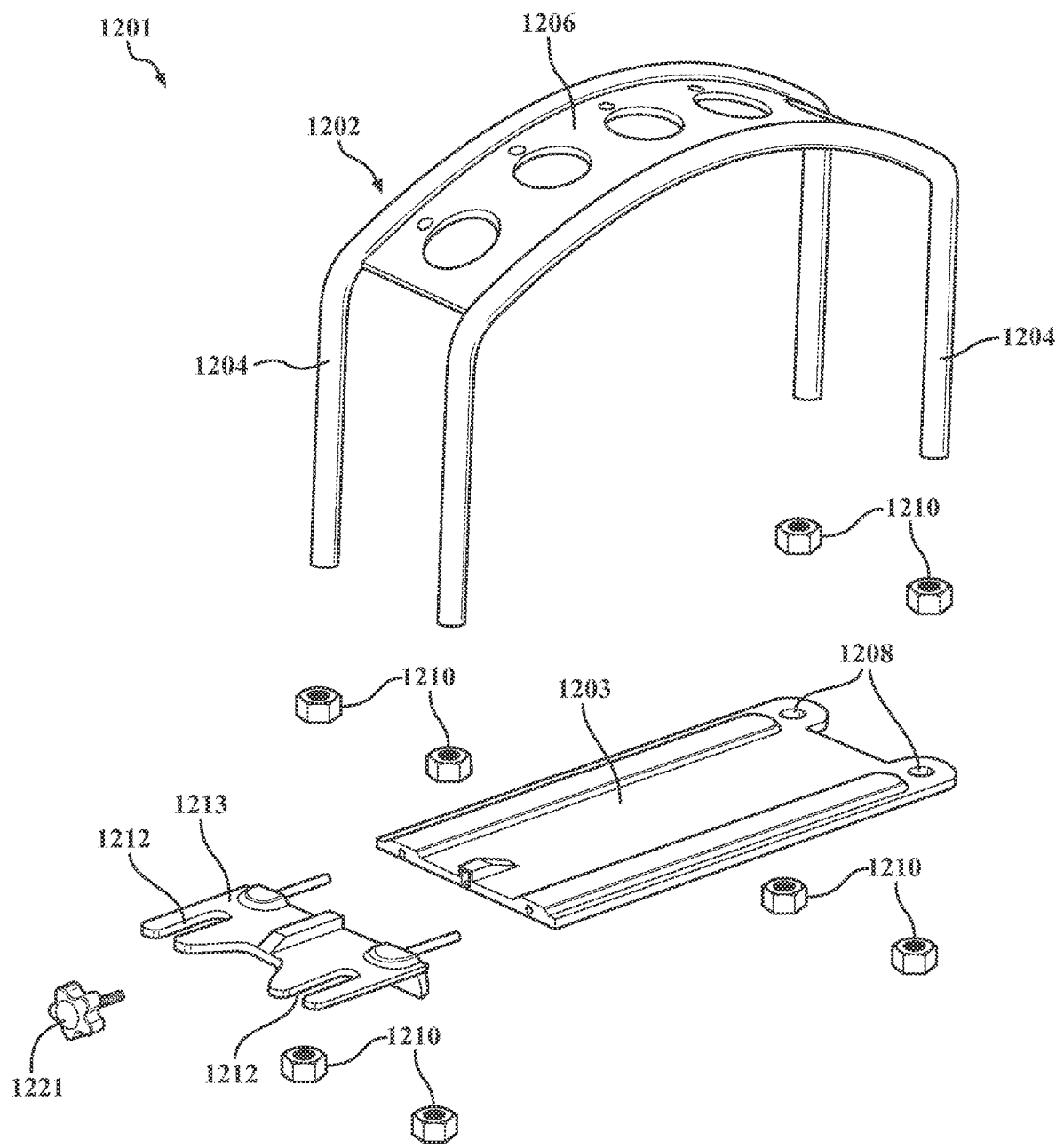
FIG. 12A-12E illustrate a second embodiment table mount for a robotic arm used for robotically assisted surgery.
Figure 12B:
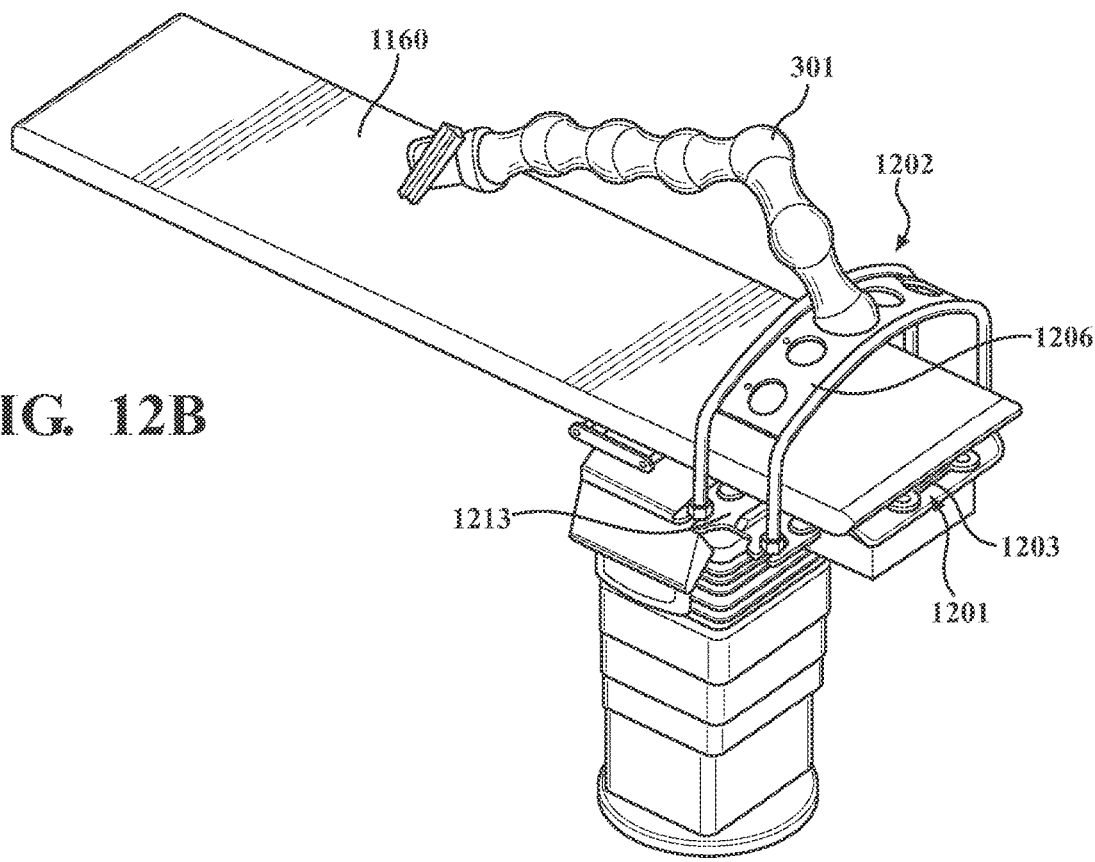
Figure 12C:
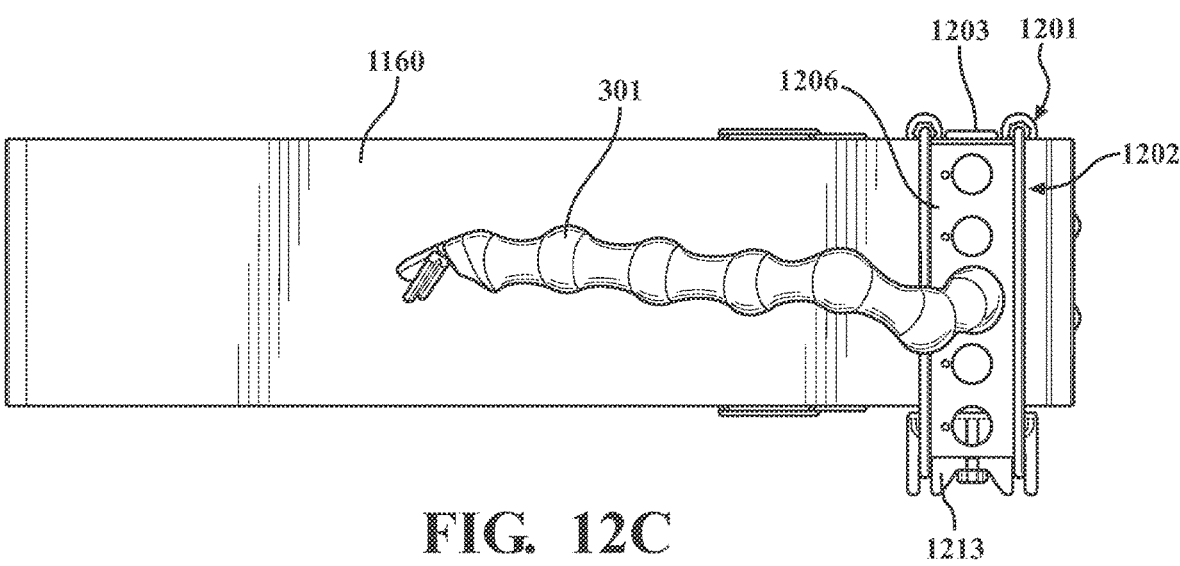
Figure 12D:
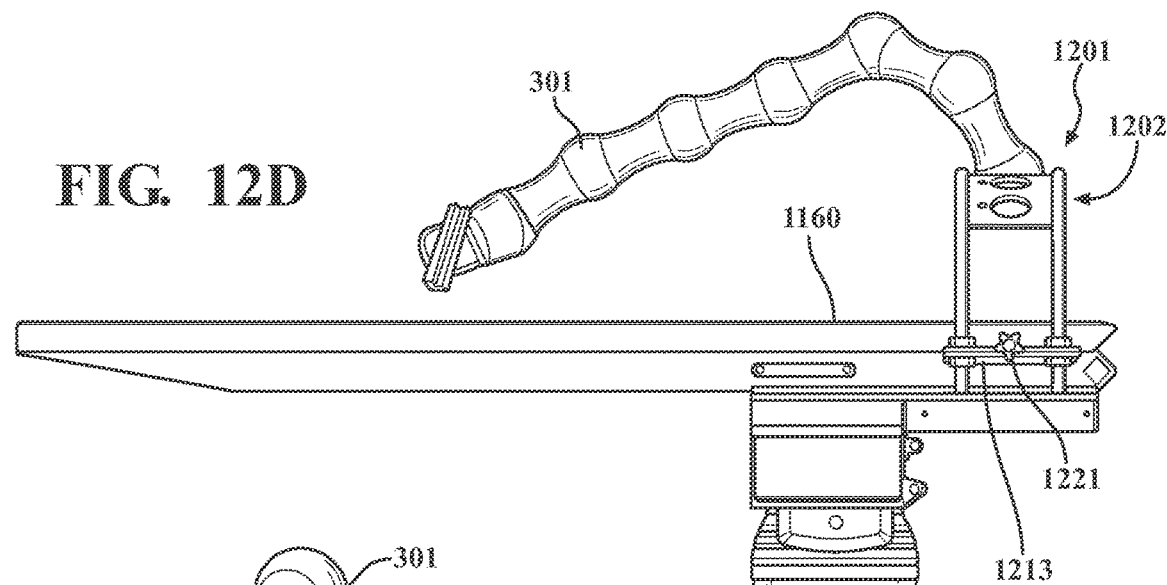

As shown in FIG. 12A, the table mount 1201 may include a generally flat plate member 1203 that may be placed on a surgical tabletop 1108. As in the embodiment of FIGS. 11A-11E, the plate member 1203 may be placed across the width of the surgical tabletop 1108, and one or more tabletop pads 1110 may be placed over the top surface of the plate member 1103. The weight of the patient on the tabletop pad 1110 and plate member 1203 may provide additional ballast to improve the stability of the table mount 1201 and robotic arm 301.

Figure 12E:
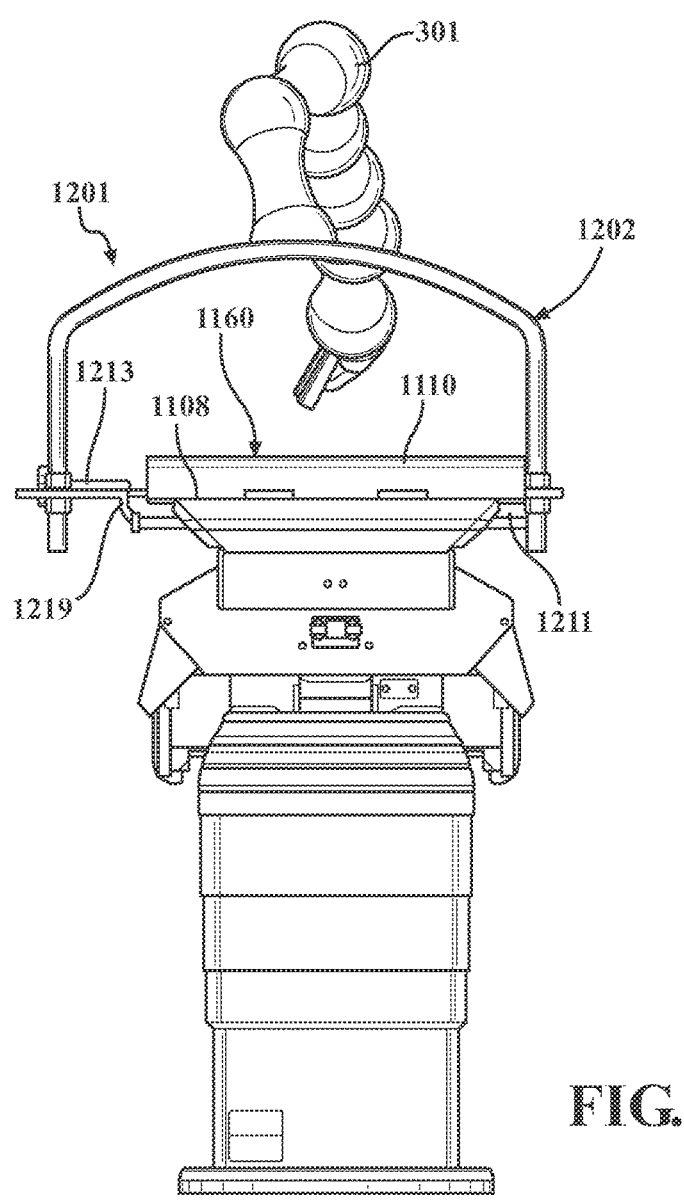

The table mount 1201 may include a clamping mechanism that fastens the table mount 1201 across the width of the surgical table 1160. A reciprocating portion 1213 of the plate member 1203 may enable the table mount to be adjusted to accommodate different table widths. As shown in FIG. 12E, a first projection 1211 may extend from the bottom surface of the plate member 1203 and abut against a structural element of the surgical table 1160. A second projection 1219 may extend from the bottom surface of the reciprocating portion 1213 of the plate member 1203 and abut against a structural element on the opposite side of the table 1160. The table mount 1201 may be clamped to the table 1160 by turning a knob 1221 (see FIG. 12A) or similar mechanism that tightens the first and second projections 1211, 1219 against opposite sides of the table 1160.

The bridge section 1202 in this embodiment include a set of four vertical support members 1204 extending from the plate member 1203 and a mounting surface 1206 supported above the table 1160 by the support members 1204. In this embodiment, the mounting surface 1206 has an arch shape, although it will be understood that the mounting surface may be flat. Two of the support members 1204 may extend through openings 1208 in the periphery of the plate member 1203. A plurality of fasteners 1210 (e.g., nuts) may be used to secure the support members 1204 within the openings 1208. The other two support members 1204 may extend through slots 1212 in the reciprocating portion 1213 of the plate member 1203. A plurality of fasteners 1210 (e.g., nuts) may be used to secure the support members 1204 within the slots 1212. The height of the mounting surface 1206 above the top surface of the table 1160 may be adjusted by varying the length of the support members 1204 extending above the plate member 1203.

FIGS. 12B-12E illustrate the table mount 1201 supporting a robotic arm 301 above the surgical table 1160. A robotic arm 301 may be mounted at various positions on the mounting surface 1206. In embodiments, the base end of the robotic arm 301 may be mounted to a moveable carriage (e.g., similar to carriage 360 shown in FIGS. 1A-1D), and the carriage with the robotic arm 301 may be slideable over the bridge section 1202 to reposition the robotic arm 301. A table mount 1201 as illustrated and described above may be used to mount other items to a surgical table, such as surgical tools, instrument trays, cameras, monitors/displays, light sources, etc.

In embodiments, multiple table mounts 1101, 1201 as shown and described above may be attached to a surgical table. A plurality of table mounts 1101, 1201 may be bridged by one or more connecting members (e.g., cross-bar(s), truss(es), etc.) that may extend over or adjacent to the surgical table, and one or more items, such as robotic arm(s), surgical instrument(s), instrument tray(s), camera(s), lighting, monitor screen(s), etc., may be mounted to a connecting member.

Figure 13:
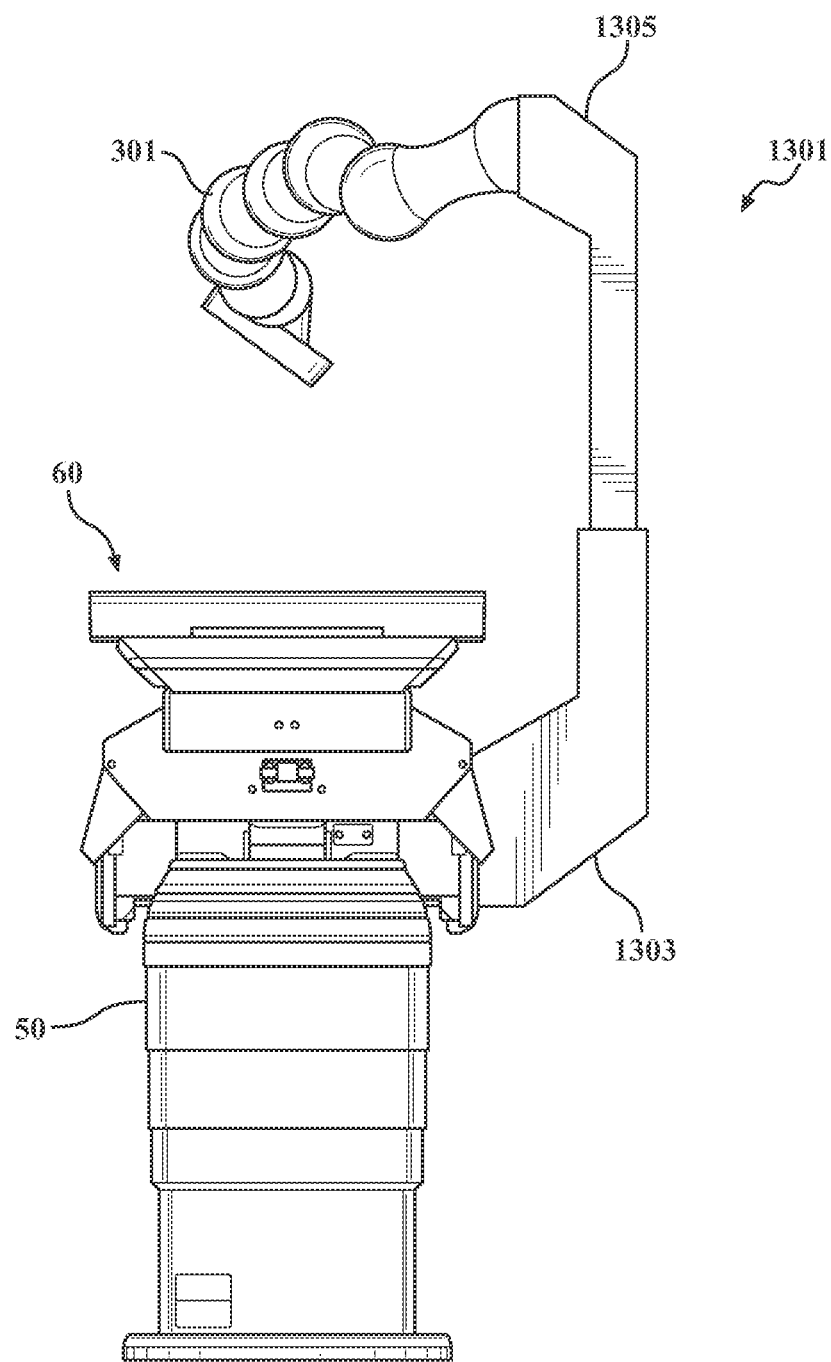
FIG. 13 illustrates a mounting apparatus for mounting a robotic arm to a support column of a surgical table.

FIG. 13 illustrates another embodiment of a table mount for a surgical robotic arm. In this embodiment, the robotic arm 301 is mounted to a column 50 that supports the surgical table 60 above the floor. The mounting apparatus 1301 in this embodiment includes a support element 1303 that is fixed to the column 50 beneath the table 60 and a support arm 1305 that extends up from the support element 1303 above the surface of the table 60. The robotic arm 301 may be mounted to the support arm 1305. In embodiments, the mounting apparatus 1301 may be adjustable such that the robotic arm 301 may be mounted adjacent to either side or optionally to at least one end of the table 60. The mounting apparatus 1301 may also be used to mount an optical sensor device for a motion tracking system.

Figure 14:
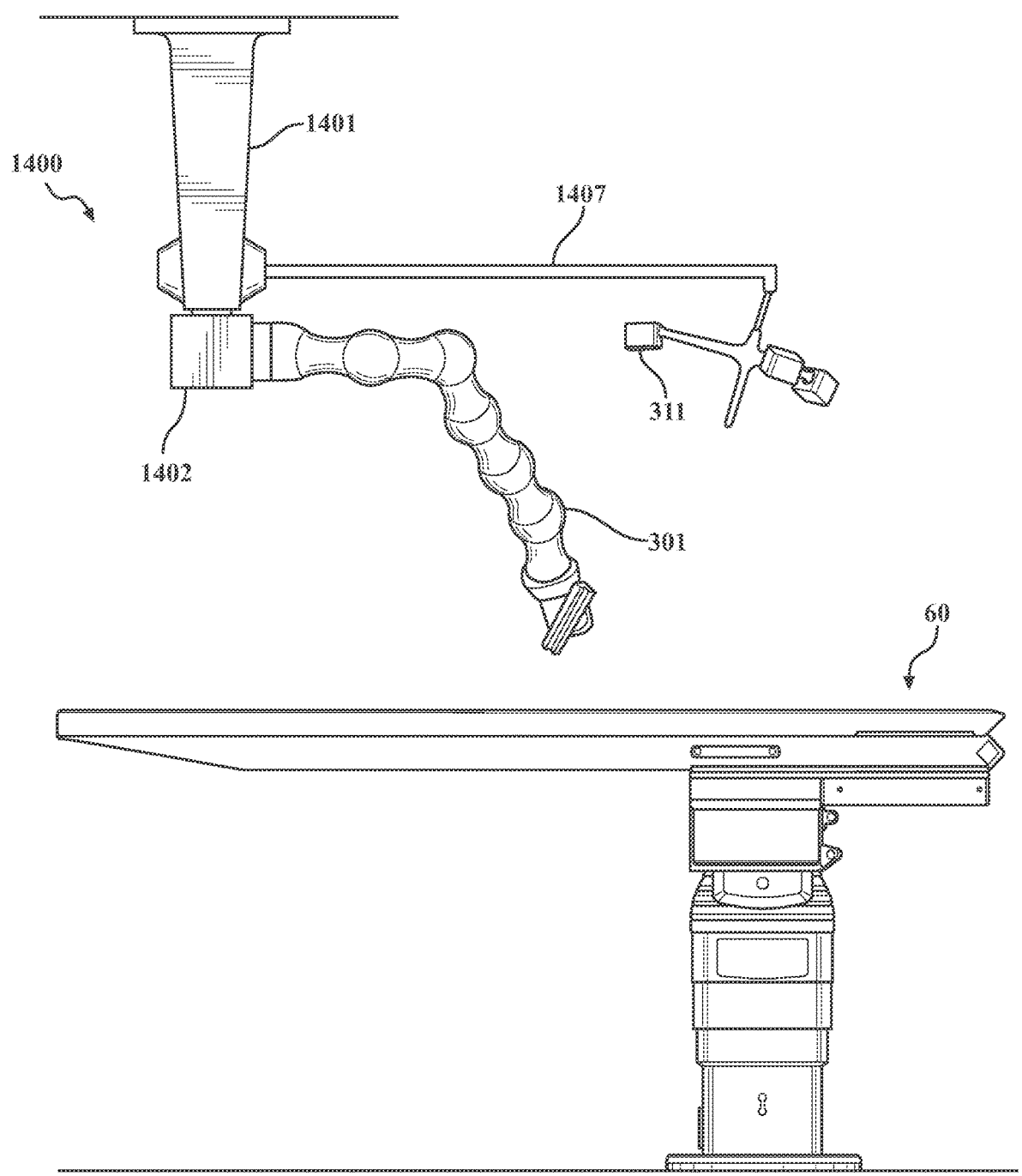
FIG. 14 illustrates a ceiling mount for a robotic arm used for robotically assisted surgery.

FIG. 14 illustrates an embodiment of a ceiling mount 1400 for a surgical robotic arm 301. The ceiling mount 1400 includes a support member 1401 that extends vertically downwards from the ceiling. The base end 304 of the robotic arm 301 may be mounted to an attachment point 1402 on the support member 1401 such that the robotic arm 301 may extend to reach a patient on a surgical table 60. In some embodiments, the height of the attachment point 1402 for the robotic arm 301 may be adjustable, such as by telescoping the support member 1401 towards or away from the ceiling. The attachment point 1402 may also be rotatable with respect to the support member 1401. In some embodiments, the entire support member 1401 may be moveable along tracks on or within the ceiling. A support arm 1407 for an optical sensor device 311 of a motion tracking system may be also attached to the support member 1401 as shown in FIG. 14.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A surgical system comprising:
    an imaging device having a gantry and a base;
    a robotic arm having a base end, an end effector, and a plurality of actuators configured to articulate the end effector relative to the base end; and
    a mobile shuttle for mounting the robotic arm proximate to the imaging device, the mobile shuttle comprising:
        a mobile base configured to move the shuttle to a position adjacent to the imaging device, the mobile base including:
            a pair of base rails spaced apart from one another and moveable adjacent to first and second sides of the base of the imaging device,
            a plurality of wheels attached to the mobile base, wherein at least a portion of the wheels are attached to the pair of base rails, and
            a connecting member extending between the pair of base rails proximate to a first end of the mobile base, the connecting member comprising a raised bridge portion moveable over a top surface of the base of the imaging device; and
        a support member for mounting the robotic arm, the support member supported by the mobile base and extending at least partially over the gantry of the imaging device when the shuttle is moved to the position adjacent to the imaging device;
    wherein when the base end of the robotic arm is mounted to a carriage, the carriage is moveable to various positions along a length of the support member.

2. The surgical system of claim 1, wherein the carriage includes a mounting surface for mounting the base end of the robotic arm.

3. The surgical system of claim 1, wherein the support member comprises a curved rail.

4. The surgical system of claim 1, wherein the mobile shuttle comprises at least one support arm extending from the mobile base, the support member supported by the at least one support arm.

5. The surgical system of claim 4, wherein the mobile shuttle comprises at least two support arms extending from opposite sides of the base, wherein a first arm is connected to a first side of the support member and a second arm is connected to a second side of the support member.

6. The surgical system of claim 5, wherein the first and second arms are offset from the support member, the first arm is connected to the first side of the support member by a first lateral connecting portion, and the second arm is connected to a second side of the support member by a second lateral connecting portion.

7. The surgical system of claim 5, further comprising an attachment mechanism on the mobile shuttle between the imaging device and the mobile shuttle.

8. The surgical system of claim 7, wherein the attachment mechanism on the mobile shuttle is located on the support arms.

9. The surgical system of claim 1, wherein the imaging device is an x-ray imaging device.

10. A mobile mounting apparatus for a robotic arm, comprising:
    a mobile base portion;
    a pair of support arms extending upwards from the mobile base portion;
    a support member for mounting at least one robotic arm having a base end, an end effector, and a plurality of actuators configured to articulate the end effector relative to the base end, the support member extending between the support arms, wherein an open region is defined between the mobile base portion, the pair of support arms, and the support member; and
    a carriage that is moveable along the support member for mounting the robotic arm;
    wherein the open region is sized and shaped to accommodate at least a portion of an x-ray imaging device within the open region.

11. The mobile mounting apparatus of claim 10, wherein the mobile base portion comprises a pair of base rails each having wheels for transporting the mounting apparatus.

12. The mobile mounting apparatus of claim 11, wherein the mobile base portion further includes a connecting member extending between the pair of base rails.

13. The mobile mounting apparatus of claim 12, wherein the connecting member comprises a raised bridge portion having a curved profile.

14. The mobile mounting apparatus of claim 12, wherein each of the support arms extends upwards from a respective one of the pair of base rails.

15. The mobile mounting apparatus of claim 10, wherein the support member comprises a curved rail.

\* \* \* \* \*